(12) United States Patent
Doshi et al.

(10) Patent No.: US 7,735,492 B2
(45) Date of Patent: Jun. 15, 2010

(54) NASAL RESPIRATORY DEVICES

(75) Inventors: Rajiv Doshi, San Francisco, CA (US);
Motohide Hatanaka, Kiyose (JP);
Robert A. Howard, Palo Alto, CA (US)

(73) Assignee: Ventus Medical, Inc., Belmont, CA (US)

( * ) Notice: Subject to any disclaimer, the term of this patent is extended or adjusted under 35 U.S.C. 154(b) by 1208 days.

(21) Appl. No.: 11/298,640

(22) Filed: Dec. 8, 2005

(65) Prior Publication Data

US 2006/0150979 A1    Jul. 13, 2006

Related U.S. Application Data

(60) Provisional application No. 60/634,715, filed on Dec. 8, 2004.

(51) Int. Cl.
*A61M 15/08*    (2006.01)

(52) U.S. Cl. .................................. 128/207.18

(58) Field of Classification Search ............ 128/207.18, 128/206.11, 205.29, 205.27, 200.24, 206.15, 128/206.18, 204.11

See application file for complete search history.

(56) References Cited

U.S. PATENT DOCUMENTS

| | | | |
|---|---|---|---|
| 628,111 A | 7/1899 | McHatton |
| 669,098 A | 3/1901 | Overshiner |
| 675,275 A | 5/1901 | Gunning |
| 746,869 A | 12/1903 | Moulton |
| 774,446 A | 11/1904 | Moulton |
| 810,617 A | 1/1906 | Carence |
| 1,819,884 A | 8/1931 | Fores |
| 2,198,959 A | 4/1940 | Clarke |
| 2,237,954 A | 4/1941 | Wilson |
| 2,264,153 A | 11/1941 | Rowe |
| 2,274,886 A | 3/1942 | Carroll |
| 2,282,681 A | 5/1942 | Stotz |
| 2,335,936 A | 12/1943 | Hanlon |
| 2,433,565 A | 12/1947 | Korman |
| 2,448,724 A | 9/1948 | McGovney |

(Continued)

FOREIGN PATENT DOCUMENTS

EP    1 157 663 A1    11/2001

(Continued)

OTHER PUBLICATIONS

Doshi et al.; U.S. Appl. No. 12/329,271 entitled "Packaging and dispensing nasal devices," filed Dec. 5, 2008.

(Continued)

*Primary Examiner*—Patricia M Bianco
*Assistant Examiner*—Tarla R Patel
(74) *Attorney, Agent, or Firm*—Shay Glenn LLP

(57) ABSTRACT

Described here are methods, devices, and kits for altering the flow of air in a respiratory cavity such as the nostrils of the nose. These methods and devices may be useful for affecting a physiologic benefit in patients suffering from a variety of medical diseases, particularly those that may benefit from "pursed-lip" breathing and non-invasive ventilation, such as COPD, heart failure, sleep apnea, and other medical disorders. The devices are typically removable devices that may be placed over or in a respiratory cavity to increase resistance to airflow within the respiratory cavity. Resistance to expiration may be selectively increased relative to inspiration. Removable nasal devices are described.

31 Claims, 23 Drawing Sheets

U.S. PATENT DOCUMENTS

| | | | |
|---|---|---|---|
| 2,672,138 A | 3/1954 | Carlock |
| 2,751,906 A | 6/1956 | Irvine |
| 2,777,442 A | 1/1957 | Zelano |
| 3,145,711 A | 8/1964 | Beber |
| 3,370,305 A | 2/1968 | Goott et al. |
| 3,451,392 A | 6/1969 | Cook et al. |
| 3,463,149 A | 8/1969 | Albu |
| 3,513,839 A | 5/1970 | Vacante |
| 3,556,122 A | 1/1971 | Laerdal |
| 3,695,265 A | 10/1972 | Brevik |
| 3,710,799 A | 1/1973 | Caballero |
| 3,722,509 A | 3/1973 | Nebel |
| 3,747,597 A | 7/1973 | Olivera |
| 3,884,223 A | 5/1975 | Keindl |
| 3,902,621 A | 9/1975 | Hidding |
| 4,004,584 A | 1/1977 | Geaney |
| 4,030,491 A | 6/1977 | Mattila |
| 4,040,428 A | 8/1977 | Clifford |
| 4,054,134 A | 10/1977 | Kritzer |
| 4,062,358 A | 12/1977 | Kritzer |
| 4,143,872 A | 3/1979 | Havstad et al. |
| 4,226,233 A | 10/1980 | Kritzer |
| 4,240,420 A | 12/1980 | Riaboy |
| 4,267,831 A * | 5/1981 | Aguilar | 128/203.14 |
| 4,327,719 A | 5/1982 | Childers |
| RE31,040 E | 9/1982 | Possis |
| 4,354,489 A | 10/1982 | Riaboy |
| 4,403,616 A | 9/1983 | King |
| 4,456,016 A | 6/1984 | Nowacki et al. |
| 4,487,207 A | 12/1984 | Fitz |
| 4,533,137 A | 8/1985 | Sonne |
| 4,582,058 A | 4/1986 | Depel et al. |
| 4,601,465 A | 7/1986 | Roy |
| 4,640,277 A | 2/1987 | Meyer et al. |
| 4,739,987 A | 4/1988 | Nicholson |
| 4,822,354 A | 4/1989 | Elosegui et al. |
| 4,854,574 A | 8/1989 | Larson et al. |
| 4,862,903 A | 9/1989 | Campbell |
| 4,908,028 A | 3/1990 | Colon et al. |
| 4,973,047 A | 11/1990 | Norell |
| 4,979,505 A | 12/1990 | Cox |
| 4,984,302 A | 1/1991 | Lincoln |
| 4,984,581 A | 1/1991 | Stice |
| 5,033,312 A | 7/1991 | Stupecky |
| 5,038,621 A | 8/1991 | Stupecky |
| 5,059,208 A | 10/1991 | Coe et al. |
| 5,078,739 A | 1/1992 | Martin |
| 5,092,781 A | 3/1992 | Casciotti et al. |
| 5,117,820 A | 6/1992 | Robitaille |
| 5,197,980 A | 3/1993 | Gorshkov et al. |
| 5,255,687 A | 10/1993 | McKenna |
| 5,383,470 A | 1/1995 | Kolbly |
| 5,385,542 A | 1/1995 | Rawlings |
| 5,391,205 A | 2/1995 | Knight |
| 5,392,773 A | 2/1995 | Bertrand |
| 5,394,867 A | 3/1995 | Swann |
| 5,415,660 A | 5/1995 | Campbell et al. |
| 5,425,359 A | 6/1995 | Liou |
| 5,459,544 A | 10/1995 | Emura |
| 5,522,382 A | 6/1996 | Sullivan et al. |
| 5,562,641 A | 10/1996 | Flomenblit et al. |
| 5,568,808 A | 10/1996 | Rimkus |
| 5,607,469 A | 3/1997 | Frey |
| 5,649,533 A | 7/1997 | Oren |
| 5,665,104 A | 9/1997 | Lee |
| 5,740,798 A | 4/1998 | McKinney |
| 5,743,256 A | 4/1998 | Jalowayski |
| 5,763,979 A | 6/1998 | Mukherjee et al. |
| 5,775,335 A | 7/1998 | Seal |
| 5,782,896 A | 7/1998 | Chen et al. |
| 5,797,920 A | 8/1998 | Kim |
| 5,823,187 A | 10/1998 | Estes et al. |
| 5,865,170 A | 2/1999 | Moles |
| 5,876,434 A | 3/1999 | Flomenblit et al. |
| 5,890,998 A | 4/1999 | Hougen |
| 5,899,832 A | 5/1999 | Hougen |
| 5,910,071 A | 6/1999 | Hougen |
| 5,911,756 A | 6/1999 | Debry |
| 5,947,119 A * | 9/1999 | Reznick | 128/204.12 |
| 5,954,766 A | 9/1999 | Zadno-Azizi et al. |
| 5,957,978 A | 9/1999 | Blom |
| 5,992,006 A | 11/1999 | Datsikas |
| 6,004,342 A | 12/1999 | Filis |
| 6,083,141 A | 7/2000 | Hougen |
| D430,667 S | 9/2000 | Rome |
| 6,119,690 A | 9/2000 | Pantaleo |
| 6,165,133 A | 12/2000 | Rapoport et al. |
| 6,177,482 B1 | 1/2001 | Cinelli et al. |
| 6,258,100 B1 | 7/2001 | Alferness et al. |
| 6,287,290 B1 | 9/2001 | Perkins et al. |
| 6,293,951 B1 | 9/2001 | Alferness et al. |
| 6,369,126 B1 | 4/2002 | Cinelli et al. |
| 6,398,775 B1 | 6/2002 | Perkins et al. |
| 6,439,233 B1 | 8/2002 | Geertsema |
| 6,484,725 B1 | 11/2002 | Chi |
| 6,500,095 B1 | 12/2002 | Hougen |
| 6,510,846 B1 | 1/2003 | O'Rourke |
| 6,527,761 B1 * | 3/2003 | Buch et al. | 604/516 |
| 6,561,188 B1 | 5/2003 | Ellis |
| 6,562,057 B2 | 5/2003 | Santin |
| 6,568,387 B2 | 5/2003 | Davenport et al. |
| 6,581,598 B1 | 6/2003 | Foran et al. |
| 6,585,639 B1 | 7/2003 | Kotmel et al. |
| 6,592,594 B2 | 7/2003 | Rimbaugh et al. |
| 6,592,995 B2 | 7/2003 | Topolkaraev et al. |
| 6,595,215 B2 | 7/2003 | Wood |
| 6,626,172 B1 | 9/2003 | Karow et al. |
| 6,626,179 B1 * | 9/2003 | Pedley | 128/857 |
| 6,631,721 B1 | 10/2003 | Salter et al. |
| 6,679,264 B1 | 1/2004 | Deem et al. |
| 6,694,979 B2 | 2/2004 | Deem et al. |
| 6,722,360 B2 | 4/2004 | Doshi |
| 6,726,598 B1 | 4/2004 | Jarvis et al. |
| 6,737,160 B1 | 5/2004 | Full et al. |
| 6,769,432 B1 | 8/2004 | Keifer |
| 6,776,162 B2 | 8/2004 | Wood |
| 6,848,446 B2 | 2/2005 | Noble |
| 6,863,066 B2 | 3/2005 | Ogle |
| 6,872,439 B2 | 3/2005 | Fearing et al. |
| 6,921,574 B2 | 7/2005 | Cinelli et al. |
| 6,997,177 B2 | 2/2006 | Wood |
| 7,011,723 B2 | 3/2006 | Full et al. |
| 7,047,969 B2 | 5/2006 | Noble |
| 7,156,098 B2 | 1/2007 | Dolezal et al. |
| 7,175,723 B2 | 2/2007 | Jones et al. |
| 7,178,524 B2 | 2/2007 | Noble |
| 7,201,169 B2 | 4/2007 | Wilkie et al. |
| 7,263,996 B2 | 9/2007 | Yung Ho |
| 2001/0037808 A1 | 11/2001 | Deem et al. |
| 2001/0051799 A1 | 12/2001 | Ingenito |
| 2001/0056274 A1 | 12/2001 | Perkins et al. |
| 2002/0062120 A1 | 5/2002 | Perkins et al. |
| 2002/0077593 A1 | 6/2002 | Perkins et al. |
| 2002/0112729 A1 | 8/2002 | DeVore et al. |
| 2003/0024527 A1 | 2/2003 | Ginn |
| 2003/0050648 A1 | 3/2003 | Alferness et al. |
| 2003/0070682 A1 | 4/2003 | Wilson et al. |
| 2003/0083671 A1 | 5/2003 | Rimbaugh et al. |
| 2003/0106555 A1 | 6/2003 | Tovey |
| 2003/0106556 A1 * | 6/2003 | Alperovich et al. | 128/206.11 |
| 2003/0140925 A1 | 7/2003 | Sapienza et al. |
| 2003/0154988 A1 | 8/2003 | DeVore et al. |
| 2003/0158515 A1 | 8/2003 | Gonzalez et al. |
| 2003/0195552 A1 | 10/2003 | Santin |

| | | |
|---|---|---|
| 2003/0209247 A1 | 11/2003 | O'Rourke |
| 2004/0016432 A1 | 1/2004 | Genger et al. |
| 2004/0020492 A1 | 2/2004 | Dubrul et al. |
| 2004/0020493 A1 | 2/2004 | Wood |
| 2004/0055606 A1 | 3/2004 | Hendricksen et al. |
| 2004/0112379 A1 | 6/2004 | Djupesland |
| 2004/0194779 A1 | 10/2004 | Doshi |
| 2004/0254491 A1 | 12/2004 | Ricciardelli |
| 2004/0261791 A1 | 12/2004 | Horian |
| 2004/0261798 A1 | 12/2004 | Rimkus |
| 2005/0011524 A1 | 1/2005 | Thomlinson et al. |
| 2005/0021073 A1 | 1/2005 | Santin et al. |
| 2005/0033344 A1 | 2/2005 | Dillard et al. |
| 2005/0051170 A1 | 3/2005 | Koo |
| 2005/0284479 A1 | 12/2005 | Schrader et al. |
| 2006/0085027 A1 | 4/2006 | Santin et al. |
| 2006/0144398 A1 | 7/2006 | Doshi et al. |
| 2006/0150978 A1 | 7/2006 | Doshi et al. |
| 2007/0051364 A1 | 3/2007 | Jacobson et al. |
| 2007/0095349 A1 | 5/2007 | Hansmann et al. |
| 2007/0277832 A1 | 12/2007 | Doshi et al. |
| 2007/0283962 A1 | 12/2007 | Doshi et al. |
| 2007/0295338 A1 | 12/2007 | Loomis et al. |

FOREIGN PATENT DOCUMENTS

| | | |
|---|---|---|
| EP | 1205203 A2 | 5/2002 |
| GB | 2324729 A | 11/1998 |
| RU | 2048820 C1 | 11/1995 |
| SU | 1586709 A1 | 8/1990 |
| WO | WO 90/12614 A1 | 11/1990 |
| WO | WO 95/17220 A1 | 6/1995 |
| WO | WO 95/33520 A1 | 12/1995 |
| WO | WO 99/03395 A1 | 1/1999 |
| WO | WO 00/29066 A1 | 5/2000 |
| WO | WO 00/50121 A1 | 8/2000 |
| WO | WO 00/67848 A1 | 11/2000 |
| WO | WO-01/02042 A1 | 1/2001 |
| WO | WO-01/13839 A1 | 3/2001 |
| WO | WO-01/13908 A2 | 3/2001 |
| WO | WO-01/13908 A3 | 3/2001 |
| WO | WO 01/49371 A2 | 7/2001 |
| WO | WO-01/87170 A1 | 11/2001 |
| WO | WO 01/89381 A1 | 11/2001 |
| WO | WO-02/38038 A2 | 5/2002 |
| WO | WO-02/38038 A3 | 5/2002 |
| WO | WO-03/022124 A2 | 3/2003 |
| WO | WO-03/022124 A3 | 3/2003 |
| WO | WO-03/034927 A1 | 5/2003 |
| WO | WO 2004/084998 A1 | 10/2004 |
| WO | WO-2006/063339 A2 | 6/2006 |

OTHER PUBLICATIONS

Doshi et al.; U.S. Appl. No. 12/329,895 entitled "Delayed resistance nasal devices and methods of use," filed Dec. 8, 2008.

Doshi et al.; U.S. Appl. No. 12/364,264 entitled "CPAP interface and backup devices," filed Feb. 2, 2009.

Doshi et al.; U.S. Appl. No. 12/369,681 entitled "Nasal devices," filed Feb. 11, 2009.

Sather et al.; U.S. Appl. No. 12/405,837 entitled "Nasal devices with noise-reduction and methods of use," filed Mar. 17, 2009.

Dillard, D. et al. (Jun. 2002). "Evaluation of a Novel Intra-bronchial Valve to Produce Lung Volume Reduction," *World Congress of Bronchology*, Boston, MA, two pages.

Mahadevia, A.K. et al. (1983). "Effects of Expiratory Positive Airway Pressure on Sleep-induced Respiratory Abnormalities in Patients with Hypersomnia-Sleep Apnea Syndrome," *Am. Rev. Respir. Dis.* 128:708-711.

Doshi et al; U.S. Appl. No. 11/811,339 entitled "Nasal devices," filed Jun. 7, 2007.

Doshi et al; U.S. Appl. No. 11/941,913 entitled "Nasal device applicators," filed Nov. 16, 2007.

Doshi et al; U.S. Appl. No. 11/941,915 entitled "Adjustable nasal devices," filed Nov. 16, 2007.

Doshi, Rajiv; U.S. Appl. No. 12/014,060 entitled "Methods and devices for improving breathing in patients with pulmonary disease," filed Jan. 14, 2008.

http://chinookmed.com/index.cfm/fa/product.display &Product_ID=275.

Sather et al.; U.S. Appl. No. 12/044,868 entitled "Respiratory sensor adapters for nasal devices," filed Mar. 7, 2008.

Pierce et al.; U.S. Appl. No. 12/141,875 entitled "Adhesive nasal respiratory devices," filed Jun. 18, 2008.

Hakel et al.; Nasal obturator for velopharyngeal dysfunction in dysarthria: technical report on a one-way valve; Journal of Medical Speech-Language Pathology; vol. 12; No. 4; pp. 155-159; 2004.

Ferdinand et al.; U.S. Appl. No. 12/485,750 entitled "Adjustable resistance nasal devices," filed Jun. 16, 2009.

\* cited by examiner

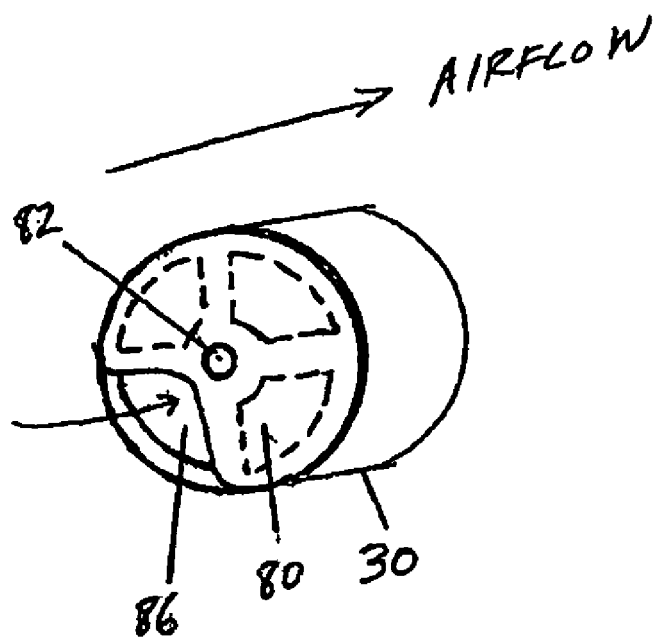
FIG. 17a
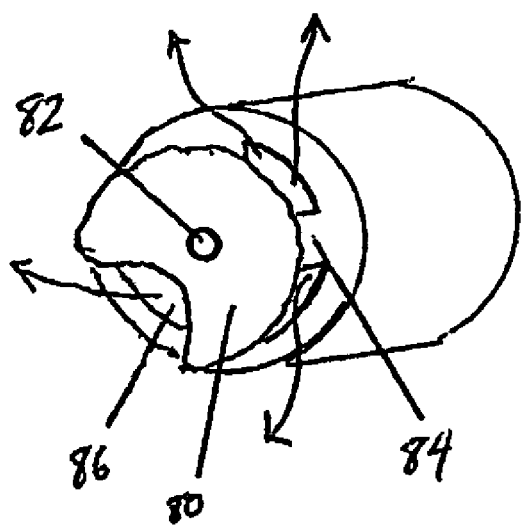
FIG. 17b

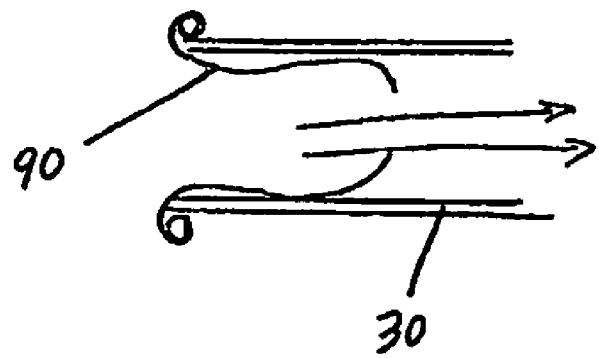
FIG. 18a
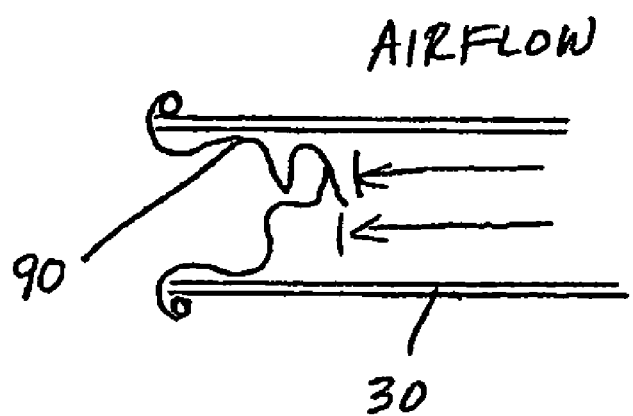
FIG. 18b

NASAL RESPIRATORY DEVICES

CROSS-REFERENCE TO RELATED APPLICATIONS

The present invention is related and claims priority to the U.S. Provisional Patent Application Ser. No. 60/634,715, filed Dec. 8, 2004. The disclosure of which is herein incorporated by reference in its entirety.

TECHNICAL FIELD

The devices, methods, and kits described herein relate generally to the field of medicine and more particularly to the fields of cardiovascular medicine, sleep medicine, pulmonology, gastroenterology, and internal medicine. In this regard, the devices, methods, and kits described may be useful in the treatment of diseases including heart failure, hypertension, sleep apnea and other sleep disorders, snoring, chronic obstructive pulmonary disease (COPD), gastroesophageal reflux disease, and various inflammatory diseases, among others.

BACKGROUND

Numerous disease states could benefit from the modification of patient respiration, including heart failure, sleep apnea and other sleep disorders, hypertension, snoring, chronic obstructive pulmonary disease (COPD), bronchitis, asthma, and many others.

Heart failure, or congestive heart failure (CHF), is a common clinical syndrome that represents the end-stage of a number of pulmonary and cardiac disease states. Heart failure is a degenerative condition that occurs when the heart muscle weakens and the ventricle no longer contracts normally. The heart can then no longer adequately pump blood to the body including the lungs. This may lead to exercise intolerance, or may cause fluid retention with subsequent shortness of breath or swelling of the feet. Over four million people are diagnosed with heart failure in the United States alone. Morbidity and mortality in patients with heart failure is high.

Sleep apnea is defined as the temporary absence or cessation of breathing during sleep. Airflow must be absent for some period of time longer than the usual inter-breath interval, typically defined as ten seconds for adults and eight seconds (or more than two times the normal respiratory cycle time) for infants. There are three general varieties of sleep apnea: central, obstructive, and mixed. In central sleep apnea, the patient makes no effort to breathe. In obstructive apnea, ventilatory effort is present, but no airflow results, because of upper airway closure. In mixed apnea, there is initially no ventilatory effort (suggestive of central sleep apnea), but an obstructive sleep apnea pattern becomes evident when ventilatory effort resumes. Finally, hypopnea is a temporary decrease in inspiratory airflow that is out of proportion to the individual's effort or metabolic needs. The terms sleep apnea and/or sleep disordered breathing may refer to hypopnea.

Hypertension refers to elevated blood pressure, and is a very common disease. Hypertension is characterized by elevated systolic and/or diastolic blood pressures. Despite the prevalence of hypertension and its associated complications, control of the disease is far from adequate. Only a third of people with hypertension control their blood pressure adequately. This failure reflects the inherent problem of maintaining long-term therapy for a usually asymptomatic condition, particularly when the therapy may interfere with the patient's quality of life, and when the immediate benefits of the therapy are not be obvious to the patient.

Chronic obstructive pulmonary disease (COPD) includes chronic bronchitis, emphysema and asthma. In both chronic bronchitis and emphysema, airflow obstruction limits the patient's airflow during exhalation. COPD is a progressive disease characterized by a worsening baseline respiratory status over a period of many years with sporadic exacerbations often requiring hospitalization. Early symptoms include increased sputum production and sporadic acute exacerbations characterized by increased cough, purulent sputum, wheezing, dyspnea, and fever. As the disease progresses, the acute exacerbations become more frequent. Late in the course of the disease, the patient may develop hypercapnia, hypoxemia, erythrocytosis, cor pulmonale with right-sided heart failure, and edema.

Chronic bronchitis is characterized by a chronic cough with sputum production leading to obstructed expiration. Pathologically, there may be mucosal and submucosal edema and inflammation and an increase in the number and size of mucus glands. Emphysema is characterized by destruction of the lung parenchyma leading to loss of elastic recoil, reduced tethering of airways, and obstruction to expiration. Pathologically, the distal airspaces are enlarged.

Asthma is another chronic lung condition, characterized by difficulty in breathing. People with asthma have extra-sensitive or hyper-responsive airways. The airways react by obstructing or narrowing when they become inflamed or irritated. This makes it difficult for the air to move in and out of the airways, leading to respiratory distress. This narrowing or obstruction can lead to coughing, wheezing, shortness of breath, and/or chest tightness. In some cases, asthma may be life threatening.

In all of these diseases, current medical and surgical therapies are not completely effective, and there is considerable room for improvement. Two therapies that are used to treat these diseases are pulmonary rehabilitation (including pursed-lip breathing) and non-invasive mechanical ventilation.

Pulmonary rehabilitation is frequently used to treat patients suffering from a variety of medical ailments such as those mentioned. For example, COPD patients are taught new breathing techniques that reduce hyperinflation of the lungs and relieve expiratory airflow obstruction. One of the goals of this training is to reduce the level of dyspnea. Typically, these new breathing techniques include diaphragmatic and pursed-lip breathing. Pursed-lip breathing involves inhaling slowly through the nose and exhaling through pursed-lips (as if one were whistling), taking two or three times as long to exhale as to inhale. Most COPD patients instinctively learn how to perform pursed-lip breathing in order to relieve their dyspnea. Moreover, patients with asthma and other respiratory ailments, and even normal people during exercise, have been shown to use pursed-lip breathing, especially during times of exertion.

It is widely believed that producing a proximal obstruction (e.g., pursing the lips) splints open the distal airways that have lost their tethering in certain disease states. In other words, airways that would normally collapse during respiration remain open when the patient breathes through pursed-lips. Moreover, by increasing exhalation time, respiratory rate can be reduced and, in some cases, made more regular.

The medical literature has confirmed the utility of pursed-lip breathing in COPD patients. Specifically, it has been found that pursed-lip breathing by COPD patients results in a reduction in respiratory rate, an increase in tidal volumes, and an improvement of oxygen saturation. All of these effects contribute to a reduction in patient dyspnea. However, pursed-lip breathing requires conscious effort. Thus, the patient cannot breathe through pursed-lips while sleeping. As a result, the patient can still become hypoxic at night and may develop pulmonary hypertension and other sequelae as a result. Furthermore, the patient has to constantly regulate his own breathing. This interferes with his performing of other activities because the patient must pay attention to maintaining pursed-lip breathing.

Non-invasive positive pressure ventilation (NPPV) is another method of treating diseases that benefit from regulation of the patient's respiration. NPPV refers to ventilation delivered by a nasal mask, nasal prongs/pillows or face mask. NPPV eliminates the need for intubation or tracheostomy. Outpatient methods of delivering NPPV include bilevel positive airway pressure (BIPAP or bilevel) ventilator devices, or continuous positive airway pressure (CPAP) devices.

NPPV can deliver a set pressure during each respiratory cycle, with the possibility of additional inspiratory pressure support in the case of bi-level devices. NPPV has been shown to be very efficacious in such diseases as sleep apnea, heart failure, and COPD, and has become increasingly used in recent years. Many patients use CPAP or BIPAP at night while they are sleeping.

However, most patients experience difficulty adapting to nocturnal NPPV, leading to poor compliance. Mask discomfort is a very common problem for patients new to NPPV, because of the high pressures on the nose, mouth, and face, and because of uncomfortably tight straps. Nasal congestion and dryness are also common complaints that may vary by season. The nasal bridge can become red or ulcerated due to excessive mask tension. Eye irritation and acne can also result. Still other patients experience abdominal distention and flatulence. Finally, air leakage through the mouth is also very common in nasal NPPV patients, potentially leading to sleep arousals.

Both pursed-lip breathing and the use of NPPV have been shown to offer significant clinical benefits to patients with a variety of medical illnesses, including but not limited to COPD, heart failure, pulmonary edema, sleep apnea (both central and obstructive) and other sleep disordered breathing, cystic fibrosis, asthma, cardiac valve disease, arrhythmias, anxiety, and snoring. Expiratory resistance is believed to provide the bulk of clinical improvements when using pursed-lip breathing and NPPV, through a variety of physiologic mechanisms. In contrast, inspiratory support is not believed to offer clinical benefits in many patients. For example, in COPD, expiratory resistance facilitates expiration, increases tidal volume, decreases respiratory rate, and improves gas exchange. In the case of heart failure, it is felt that positive pressure in the airways (due to expiratory resistance) reduces pulmonary edema and improves lung compliance, decreases preload and afterload, increases $pO_2$, and decreases $pCO_2$. In many disease states, expiratory resistance helps maintain a more stable respiratory rate that can have profound clinical effects to the patient.

It would therefore be desirable to have a medical device and/or procedure that mimics the effect of pursed-lip breathing and/or the benefits of non-invasive ventilation without suffering from the drawbacks described above.

BRIEF SUMMARY

Described herein are respiratory devices and methods for treating a variety of medical diseases through the use of such devices. Some versions of these devices make use of expiratory resistance to mimic the effects of pursed-lip breathing and non-invasive ventilation (with or without positive end expiratory pressure, or PEEP).

The respiratory device described herein is adapted to be removably secured in communication with a respiratory cavity. A respiratory cavity may be a nasal cavity (e.g., nostril or nasal passage) or an oral cavity (e.g., mouth or throat). The respiratory device comprises a passageway, an airflow resistor in communication with the passageway, and a holdfast for removably securing the respiratory device in communication with the respiratory cavity. The airflow resistor alters the flow of air passing within the passageway. In particular, the airflow resistor may alter the flow of air within the passageway by increasing the resistance to the flow of air in the passageway. The respiratory device may be applied or removed by the user of the device, and thus, does not need to be applied by a physician or other healthcare personnel.

In one version, the respiratory device is adapted to be removably secured in communication with a nasal cavity. The respiratory device may also comprise a rim for supporting the passageway. The rim may be, for example, a frame, a framework, or a tube comprising a material and a shape that prevents the passageway from collapsing during use, particularly when the device is used during repeated cycles of inhalation and exhalation. In some versions, the rim defines at least a portion of a wall of the passageway. However, the rim may support a passageway (or a portion of the passageway) which has another material (e.g., a medicinal or protective layer) that defines all or part of the inner lumen of the passageway.

In one version, the airflow resistor increases the resistance of air being exhaled and/or inhaled through the passageway. The airflow resistor may have an orientation, so that resistance to airflow in one direction is greater than the opposite direction. For example, the airflow resistor may increase the resistance to air exhaled through the passageway of the respiratory device without substantially increasing the resistance to air inhaled through the passageway. The airflow resistor may increase the resistance to air exhaled through the passageway of the respiratory device more than it increases the resistance to air inhaled through the passageway. Furthermore, the respiratory device may be reversible, so that in one orientation resistance to airflow through the device during inhalation is higher than resistance to airflow through the device during exhalation. By reversing the device (or by reversing the airflow resistor portion of the device), resistance to airflow through the device during exhalation is higher than resistance to airflow through the device during inhalation.

In one version, the airflow resistor decreases the resistance to air exhaled and/or inhaled through the passageway when the airflow across the airflow resistor or the air pressure differential across the airflow resistor exceeds a threshold level. Thus, for example, the respiratory device may not inhibit airflow (or not substantially inhibit airflow) in the passageway during a cough, sneeze, nose blowing or other high airflow/high pressure event. The threshold value may be determined based on measurements or approximations from a particular user. For example, the threshold may be a value above the normal peak of airflow or pressure during normal expiration. The threshold value may also be determined based on a typical value approximated from many patients This threshold pressure for example may fall within the range of 0.1 to 1000 cm $H_2O$ pressure, more preferably within the range of 0.5 and 100 cm $H_2O$ pressure, and most preferably within the range 1.0 and 50 cm $H_2O$ pressure In one version, the airflow resistor increases the resistance to air exhaled and/or inhaled through the passageway when the airflow across the airflow resistor or the air pressure differential across the airflow resistor falls below a threshold level. Thus, the respiratory device may create a PEEP (positive end expiratory pressure) effect by, for example, preventing complete exhalation based on the pressure applied against the device, if the pressure and/or airflow at the end of exhalation are below the threshold level selected. The threshold level may correspond to an air pressure differential, air pressure, or airflow measured from an individual patient, or it may correspond to a typical value, such as a typical value measured from a sample of patients. This threshold pressure for example may fall within the range of 0.1 to 150 cm $H_2O$, more preferably within the range of 0.5 to 30 cm $H_2O$, and most preferably within the range of 1.0 to 25 cm $H_2O$.

In some versions, the airflow resistor is a nested airflow resistor. Nested airflow resistors may be airflow resistors configured to alter the flow of air in the passageway under different conditions (e.g., different directions or different flow rates or pressure differentials across the resistor). For example, a nested airflow resistor may be a combination of multiple airflow resistors "nested" so that they affect the flow of air in the passageway under different conditions. Thus a first flap valve that increases the resistance to airflow in a first direction may be combined with a second flap valve that opens when the resistance to airflow in the first direction is above a threshold. In one version, the second flap valve is integral to the flap portion of the first flap valve.

Virtually any type of airflow resistor may be used with the respiratory devices described herein, including flap valves, membrane valves, hingeless valves, balloon valves, stopper-type valves, ball valves, and the like. The device may include a variety of "one-way valve structures," or other flow responsive elements that open to inspiration and close partially or completely to expiration. In one version, the airflow resistor is a flap valve. The airflow resistor may be a plate which is held within a nasal cavity that occludes some portion of the luminal cross-sectional area of the nasal cavity. The airflow resistor may selectively increase resistance to expiration while minimally or trivially increasing flow resistance to inspiration. When closing during expiration, the airflow resistor may or may not fully prevent airflow, depending on the design of the device.

In one version, the airflow resistor is configured to alter the inspiratory time:expiratory time (I:E) ratio of a user wearing the respiratory device to be between about 3:1 and about 1:10. In another version, the airflow resistor is configured to alter the inspiratory time:expiratory time ratio of a user wearing the respiratory device to be between about 1:1.5 and about 1:4. In another version, the airflow resistor is configured to alter the inspiratory time:expiratory time ratio of a user wearing the respiratory device to about 1:3.

In some versions of the respiratory device the holdfast removably secures the respiratory device in communication with a nasal cavity of a user so that at least some of the air exchanged between the nasal cavity and the external environment of a user passes through the respiratory device. The holdfast may removably secure the respiratory device to a user's nasal cavity so that all of the air exchanged between the nasal cavity and the user's external environment passes through the respiratory device. The respiratory device may be secured at least partly within the nasal cavity, or totally within the nasal cavity, or totally external to the nasal cavity, but in communication with the nasal cavity. The device may be adapted to communicate with the nasal cavity by being removably secured within or near the nares.

The respiratory device may be partly secured in the nasal cavity of a user so that an outer surface of the respiratory device exerts pressure against the nasal cavity. For example, an outer surface (e.g., the holdfast) may be oversized so that it exerts pressure against the nasal cavity.

In some versions of the respiratory device, the holdfast removably secures the respiratory device in communication with both of a user's nasal cavities (e.g., both nostrils or nasal passages). In some versions, the holdfast may removably secure the respiratory device within both of a user's nasal cavities (e.g., nostrils or nasal passages). In some versions, the holdfast removably secures the respiratory device in communication with a user's oral cavity and at least one nasal cavity.

In some versions, the respiratory device further comprises an active agent. In some versions, this active agent is a drug (e.g., a medicament). In some versions, this active agent comprises an odorant, such as a fragrance. In some versions, the active agent comprises menthol, eucalyptus oil, and/or phenol.

In some versions, the respiratory device further comprises a filter. This filter may be a movable filter, such as a filter that filters air flowing through the passageway in one direction more than another direction (e.g., the device may filter during inhalation but not expiration).

In some versions, the respiratory device further comprises a respiratory gas supply. For example, a respiratory gas supply (e.g., Oxygen, or any mixture of respiratory gases) may be used in conjunction with a respiratory device. In some versions, the respiratory device is adapted to connect to a respiratory gas supply.

In some versions, the holdfast comprises a conformable material. For example, the device may fit snugly within or against a respiratory cavity by compressing the holdfast (or a portion of the holdfast), which may expand to fit in or against the respiratory cavity securing the device in place, and preventing air exchange between the respiratory cavity and the external environment unless the air passes through the respiratory device.

Also described herein are respiratory devices adapted to removably secure to a nasal cavity comprising a passageway, a rim, and a holdfast for securing the respiratory device to at least one nasal cavity. The rim has sufficient strength to support the passageway in the open state when the device is inserted into the nasal cavity. The respiratory device may be applied or removed by the user.

Also described herein are respiratory devices adapted to be removably secured in a nasal cavity comprising a passageway, a filter within the passageway, and a holdfast for securing the respiratory device within a nasal cavity. The respiratory device may be applied or removed by a user. In one version, the filter is a movable filter for filtering air flowing through the device during either inhalation (but not exhalation) or during exhalation (but not inhalation). For example, if the movable filter filters air during inhalation, it may then move at least partly out of the path of airflow during exhalation.

Also described herein are methods of regulating $pCO_2$ in a patient comprising removably securing a respiratory device in communication with a patient's nasal cavity, wherein the respiratory device comprises an airflow resistor that inhibits expiration more than it inhibits inhalation.

Also described herein are methods of simulating pursed-lip breathing in patients comprising removably securing a respiratory device in communication with a patient's nasal cavity, wherein the respiratory device comprises an airflow resistor that inhibits expiration more than it inhibits inhalation.

Also described herein are methods of treating a sleeping disorder comprising removably securing a respiratory device in communication with a patient's nasal cavity, wherein the respiratory device comprises an airflow resistor that inhibits expiration more than it inhibits inhalation.

Also described herein are methods of treating chronic obstructive pulmonary disease comprising removably securing a respiratory device in communication with a patient's nasal cavity, wherein the respiratory device comprises an airflow resistor that inhibits expiration more than it inhibits inhalation.

Also described herein are methods of treating a cardiovascular disorder comprising removably securing a respiratory device in communication with a patient's nasal cavity, wherein the respiratory device comprises an airflow resistor that inhibits expiration more than it inhibits inhalation.

Also described herein are methods of treating a gastroenterologic disorder (such as gastroesophageal reflux disease or hiatal hernia) comprising removably securing a respiratory device in communication with a patient's nasal cavity, wherein the respiratory device comprises an airflow resistor that inhibits expiration more than it inhibits inhalation.

Also described herein are kits comprising a respiratory device as described herein and instructions on the use of the respiratory device.

In some versions, the devices are removable and are placed within the nose and/or mouth of the patient.

In some versions of the respiratory device, the device is adapted to be in communication with an oral cavity by securing substantially within the oral cavity. The same embodiments described above for respiratory devices that may be secured in communication with a nasal cavity may be used with these versions. The device may be substantially within the oral cavity when most (but not necessarily all) of the device is within the oral cavity. For example, a small portion of the device may project from the oral cavity. Of course, in some variations, a device that is substantially within the oral cavity may refer to a device that is held entirely within the oral cavity.

Some of the devices feature either non-moving parts, or moving parts that can partially obstruct the breathing passageway on expiration and minimally obstruct the breathing passageway on inspiration. That is, the direction of the airflow and the pressure differential across the valve may determine the degree of obstruction. The respiratory devices may be used during the day, night, or both. For example, these devices may be worn during sleep and/or during waking hours. Furthermore, the devices may be kept in place for long durations, such as several hours, days, or weeks.

The devices and methods described herein may be used to treat a variety of disease states, and can be inserted and removed depending on need. These devices may also comprise a positioner to assist in positioning the device in communication with a respiratory orifice such as the nasal cavities. The positioner may be attached to a device, for example, as a handle or grip. The positioner may also be a device in which the respiratory device sits until it is secured in communication with a respiratory orifice, and then the positioner may be removed, leaving the respiratory device in place.

In some versions, the respiratory device comprises a nasal device useful for treating a variety of disease states. A user may conveniently insert and remove the device depending on need.

The methods for treating patients suffering from a variety of medical ailments through the use of an expiratory resistor broadly comprise creating a resistance to expiratory flow in or around the oral and/or nasal cavities, typically within or around the mouth or the nares. The methods may comprise use of any of the devices described above. For example, airflow resistance may be created by placing a flow resistor, either one with a fixed flow resistance or one with a variable flow resistance, i.e., which is higher to expiration than inspiration.

BRIEF DESCRIPTION OF THE DRAWINGS

FIG. 7a shows the device during inhalation, and FIG. 7b shows the device during exhalation.

FIG. 15a shows the airflow resistor during higher levels of exhalation airflow and/or pressure. FIG. 15b shows the airflow resistor during lower levels of exhalation airflow and/or pressure. FIG. 15c shows the airflow resistor during inhalation.

FIGS. 17a and 17b are perspective views of a respiratory device having an airflow resistor where the airflow resistor is shown during exhalation (FIG. 17a) and inhalation (FIG. 17b), respectively.

FIGS. 18a and 18b show cross-sectional views of a respiratory device having an airflow resistor where the airflow resistor is shown during inhalation (FIG. 18a) and exhalation (FIG. 18b), respectively.

DETAILED DESCRIPTION

Figure 1:
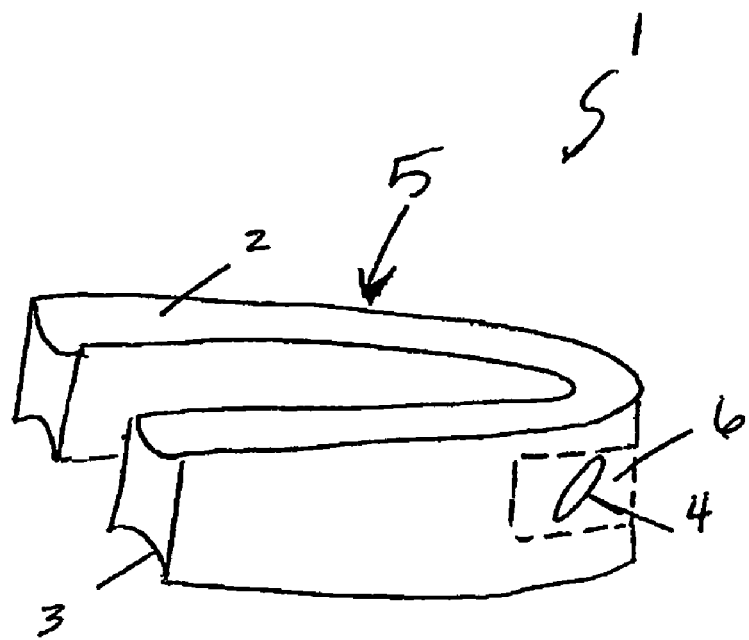
FIG. 1 is a perspective view of a respiratory device adapted for an oral cavity.

Described here are respiratory devices, kits, and methods for their use in improving respiratory and cardiovascular function. In general, the respiratory devices are referred to as respiratory devices or simply as "devices." The devices and methods described herein may be useful to treat a variety of medical disease states, and may also be useful for non-therapeutic purposes. The devices and methods described herein are not limited to the particular embodiments described. Variations of the particular embodiments may be made and still fall within the scope of the appended claims. It is also to be understood that the examples and particular embodiments described are not intended to be limiting. Instead, the scope of the present invention will be established by the appended claims.

As used in this specification, the singular forms "a," "an," and "the" include plural reference unless the context clearly dictates otherwise. Unless defined otherwise, all technical and scientific terms used herein have the same meaning as commonly understood by one of ordinary skill in the art.

Devices

The respiratory devices described herein alter airflow into and out of the lungs through a respiratory cavity such as the mouth and/or the nostrils of the nose. The respiratory devices typically include an airflow resistor capable of at least partly obstructing airflow, particularly airflow in one direction (e.g., expiration) more than the opposite direction (e.g., inhalation). In particular, the respiratory devices may be used to increase the resistance to expiration during the expiratory phase of the respiratory cycle. Many of the respiratory devices described herein may prevent collapse of airways and airflow conduits, provide a method of drug delivery, and filter air of undesirable compounds or agents.

Passageway

The respiratory devices described herein generally comprise an airflow passageway and an airflow resistor. The airflow passageway (or "passageway") generally defines a channel allowing the passage of air. The passageway may be of any suitable size or shape; however it is configured so that when the respiratory device is worn by a patient, the passageway comprises an opening leading toward the patient's lungs in fluid connection with an opening that leads away from the patient's lungs. The term "patient" is used to describe any user of the respiratory device, including users who are not using the respiratory device for therapeutic purposes. The airflow passageway may be any suitable length. For example, the passageway may be as short as the airflow resistor will allow (e.g., extending only enough to support the airflow resistor). Similarly, the airflow passageway may be longer than the space required to support the airflow resistor. For example, in versions of the respiratory device adapted for at least partial insertion into a nasal cavity, the airflow passageway way may be approximately as long as the length of an average nares. In some versions, the passageway extends the length of an average nasal chamber.

The neutral diameter of the passageway may be of any appropriate size. Neutral diameter refers to the diameter of the passageway when the device allows air to flow through the passageway without additional resistance (e.g., due to an airflow resistor). In particular, the diameter of the passageway may depend upon configuration of the respiratory device. For example, respiratory devices configured to be inserted within the nasal cavity (e.g., a nasal chamber) may have a diameter that is approximately the diameter of a narrow portion of the nasal cavity, or slightly narrower. Respiratory devices configured to be secured over an oral cavity or a nasal cavity may have passageways of larger diameters. Furthermore, the diameter of a passageway may vary across the length of the device.

The airflow passageway may comprise a dedicated structure defining the inner wall of the airflow passageway, or it may be a structural component of the device. For example, the passageway may comprise a passage wall defined by a rim. A rim may be a tube (or tunnel) of material of any appropriate thickness. The rim may also be a frame, rather than a complete tube. The rim may comprise a sufficiently rigid material so that it can support the passageway, and prevent the passageway from collapsing during use and during respiration. In some versions, the rim comprises a compressible material that may be compressed to facilitate insertion and removal, while maintaining the ability to support the passageway and prevent complete collapse of the passageway during respiration. The rim may also be somewhat compressible during respiratory flow. The airflow passageway (including a rim portion) may also serve as an attachment site for other components such as airflow resistors, filters, anchors, etc.

The rim may be any suitable shape or size. For example, the rim may comprise a ring shape or an oval shape. The rim may have an inner diameter which is equivalent to (or larger than) the diameter of the passageway. In some versions, the rim comprises a material having strength sufficient to prevent the collapse of a respiratory device that has been inserted into a nasal cavity. For example, the rim may comprise a metal, a polymer (particularly stiff polymers), etc. In some versions, the rim may comprise softer or "weaker" materials which are formed or arranged so that the final shape of the rim has sufficient strength to prevent the collapse of the respiratory device during use.

In some versions, the airflow passageway does not include a dedicated structure such as a rim. For example, the airflow passageway of the respiratory device may be a passageway through another component of the device, such as holdfast. In some versions, the airflow passageway is defined by a passageway through a holdfast.

Airflow Resistor

An airflow resistor is typically positioned in communication with at least one airflow passageway, so that at least some of the air flowing through the passageway passes the airflow resistor. Thus, an airflow resistor modulates, alters, varies, or keeps constant the amount of resistance, the degree of airflow, or the pressure differential across the device or through a passageway in the device. In some versions, the airflow resistor inhibits airflow more greatly in one direction than the opposite direction. Thus, the airflow resistor may regulate airflow to and from the lungs. Some versions of the device have a greater resistance to exhalation than to inhalation during use.

In some versions of the respiratory device, the airflow resistor comprises a valve that does not appreciably impede airflow in a certain direction (e.g., inspiration), and that partially or completely impedes airflow in the other direction (e.g., expiration). In some embodiments, the valve allows for an expiratory obstruction to be relieved if a certain degree of airflow or pressure differential across the device is achieved, as might be the case with coughing or nose blowing. For example, in some embodiments, the valve comprises a flap made of a shape memory or deformable material (e.g., an elastic material); when the pressure differential across the valve (the expiratory airflow pressure) is large enough, the flap bends upon itself, thereby relieving the obstruction. This may be important during coughing and may also facilitate the clearance of mucous and other substances during coughing. After the cough, the flap returns to its original, non-bent conformation.

Examples of different types of airflow resistors are described below and illustrated in FIGS. 6, 8, 9, 10, 11, and 13-19. Any airflow resistance device capable of altering the resistance of air (e.g., due to inspiration and/or expiration) passing through an air passageway may be used, particularly devices which selectively increase the resistance of air flow in one direction more than in the opposite direction. Valve-type airflow resistors are particularly suitable. Examples of valves which may be used as airflow resistors include: flap valves (having one or more flaps); hingeless valves; stopper-type valves; membrane-type valves; ball valves; balloon-type valves; and the like. This list is not intended to be exhaustive, and other types of selective airflow resistors may be used. Moreover, multiple airflow resistors may also be used, which may include combinations of different types of airflow resistors.

Holdfast

The respiratory device may further comprise a holdfast for releasably securing the device in communication with a nasal and/or oral cavity. The holdfast may facilitate the positioning and securing of the device in a desired location, such as over or within (e.g., substantially within) a respiratory orifice. In particular, the holdfast may allow the device to be anchored, positioned, and/or stabilized in any location that is subject to respiratory airflow such as a respiratory cavity.

Examples of respiratory cavities include nasal and oral cavities. Nasal cavities may comprise the nostrils, nares or nasal chambers, limen, vestibule, greater alar cartilage, alar fibrofatty tissue, lateral nasal cartilage, agger nasi, floor of the nasal cavity, turbinates, sinuses (frontal, ethmoid, sphenoid, and maxillary), and nasal septum. The term "nasal cavity" may refer to any sub-region of the Nasal Fossa (e.g., a single nostril, nare, or nasal chamber).

An oral cavity includes the cavity of the mouth (e.g., vestibule and mouth cavity proper), and any sub-region thereof, including or more than one of the following structures: maxilla, mandible, gums, lips, teeth, jaw, tongue, hard or soft palate and the recess or gap between the teeth/gums and the lips.

In some versions, the holdfast may also secure a seal between the respiratory device and the respiratory airway, so that at least some of the air exchanged between the outside of the patient and the respiratory airway must pass through the respiratory device. In some versions, the holdfast seals the device in communication with a respiratory cavity completely, so that all air must be exchanged through the device. In some versions, the holdfast seal is incomplete, so that only some of the air exchanged between the patient and the external environment passes through the device. As used herein, "air" may be air from environment external to the patient, or it may be any respiratory gas (e.g., pure or mixed oxygen, $CO_2$, heliox, or other gas mixtures provided to the user).

In some versions, the holdfast may comprise an anchor or anchor region.

In some embodiments, the device is to be placed by the patient or the healthcare provider in communication with an oral cavity. In this case, the holdfast may comprise any suitable mechanism for securing the device in position in communication with an oral cavity. The holdfast may comprise insertive (e.g., mouthpiece-type) and non-insertive mechanisms. A non-insertive holdfast may comprise a surface configured to mate with the outer surface of a patient's face to secure the device. For example, a holdfast may comprise an adhesive bandage, a strap, or any other structure capable of securing the device in communication with a user's respiratory cavity. The holdfast may comprise a removable region that contours to interfaces with the lips, gums, teeth, tongue and/or soft palate of the user, allowing the user to insert or remove the device as needed. Alternatively, the device can be held in place by utilizing the area in between the gums and teeth or lips.

In other embodiments, the device is to be placed by the patient or the healthcare provider in or around the nasal cavity. Holdfasts appropriate for nasal cavities may secure the device in position within a nasal cavity (e.g., through one or both nostrils) or against surrounding structures. The holdfast may comprise a shape, surface or material that secures the device in communication with a nasal cavity. For example, the holdfast may comprise a cylindrical shape that allows the device to fit securely or snugly within a nostril. The outer surface of the device may comprise a holdfast including an adhesive material. In addition to holding the device in place, the holdfast may also partially or completely seal the device in communication with the nasal cavity. The holdfast may comprise insertive and/or non-insertive mechanisms. In some versions, the holdfast comprises a mechanical connection between the device and the user, such as a clips, straps, and the like.

The holdfast may be formed from a soft or compliant material that provides a seal, and may enhance patient comfort. Furthermore, compliant materials may reduce the likelihood that the device cuts off blood flow to the part of the respiratory cavity and surrounding regions (mouth or nose) to which the device is anchored. This compliant material may be one of a variety of materials including, but not limited to, plastic, polymers, cloth, foamed, spongy, or shape memory materials. Shape materials include any that have a preferred conformation, and after being deformed or otherwise deflected or altered in shape, have tendency to return to a preferred conformation. Soft shape memory materials may include, but are not limited to, urethane, polyurethane, sponge, and others (including "foamed" versions of these materials). Alternatively, the holdfast may not be soft or compliant and may instead be a rigid structure that interfaces directly with the respiratory orifice. For example, in versions of the respiratory device configured to be used at least partly within a nasal cavity, it is understood that the device may fit completely within a nostril (or both nostrils), or may project out of the nostril, depending on the particular embodiment. In some cases, the device may be placed high enough within the nasal cavity so that it cannot be seen within the nostril. In some embodiments the device may be located completely outside of the nose, for example, in some versions the holdfast has a shape that conforms to the outside surface of the nose. Thus, the holdfast may comprise one or more straps, bands, or the like to ensure an adequate fit and/or seal maintaining the device in communication with the nasal cavity. In another embodiment the holdfast may comprise one or more projections that are inserted within the nostrils. In some versions, a device may be placed at least partly in both nostrils, and may comprise a bifurcated passageway or two passageways that the holdfast places in communication with the nasal cavity through each nostril. In this case, the inspiratory and/or expiratory airflow to and from the lungs may be regulated through each nostril separately or together. In some versions, separate devices may be placed at least partly in each nostril, and may be connected to each other and/or the patient using a clip, tether, strap, band, chain, string, or the like. Such a system would facilitate subsequent removal of the device and make migration of the devices deeper into the nasal cavity less likely. Finally, in some devices, an adhesive flap may be present to help attach the device to the inside or outside of the nose (including the nostrils), to the oral cavity, to the neck, or to the face.

Materials

Respiratory devices may be made from any appropriate material or materials. In certain embodiments, the devices include a shape memory element or elements, as part of the holdfast, in the airflow resistor, or in giving form to the passageway. Any convenient shape memory material that provides for flexibility and resumption of configuration following removal of applied force may be employed in these embodiments. For example, shape memory alloys may be used. A variety of shape memory alloys are known, including those described in U.S. Pat. Nos. 5,876,434; 5,797,920; 5,782,896; 5,763,979; 5,562,641; 5,459,544; 5,415,660; 5,092,781; 4,984,581; the disclosures of which are herein incorporated by reference in their entirety. The shape memory alloy that is employed should generally be a biocompatible alloy. Biocompatible alloys may include nickel-titanium (NiTi) shape memory alloys sold under the Nitinol™ name by Memry Corporation (Brookfield, Conn.). Also of interest are spring steel and shape memory polymeric or plastic materials, such as polypropylene, polyethylene, etc.

Rubber and polymeric materials may also be used, particularly for the holdfast or airflow resistor. For example, materials which may be used include: latex, polyethylene, polypropylene, polystyrene, polyvinyl chloride, polyvinylidene chloride, polyvinyl acetate, polyacrylate, styrene-butadiene copolymer, chlorinated polyethylene, polyvinylidene fluoride, ethylene-vinyl acetate copolymer, ethylene-vinyl acetate-vinyl chloride-acrylate copolymer, ethylene-vinyl acetate-acrylate copolymer, ethylene-vinyl acetate-vinyl chloride copolymer, nylon, acrylonitrile-butadiene copolymer, polyacrylonitrile, polyvinyl chloride, polychloroprene, polybutadiene, thermoplastic polyimide, polyacetal, polyphenylene sulfide, polycarbonate, thermoplastic polyurethane, thermoplastic resins, thermosetting resins, natural rubbers, synthetic rubbers (such as a chloroprene rubber, styrene butadiene rubber, nitrile-butadiene rubber, and ethylene-propylene-diene terpolymer copolymer, silicone rubbers, fluoride rubbers, and acrylic rubbers), elastomers (such as a soft urethane, water-blown polyurethane), and thermosetting resins (such as a hard urethane, phenolic resins, and a melamine resins).

Biocompatible materials may be used, particularly for those portions of the device (e.g., the holdfast) which may contact a user. In addition to some of the materials described above, the biocompatible materials may also include a biocompatible polymer and/or elastomer. Suitable biocompatible polymers may include materials such as: a homopolymer and copolymers of vinyl acetate (such as ethylene vinyl acetate copolymer and polyvinylchloride copolymers), a homopolymer and copolymers of acrylates (such as polypropylene, polymethylmethacrylate, polyethylmethacrylate, polymethacrylate, ethylene glycol dimethacrylate, ethylene dimethacrylate and hydroxymethyl methacrylate, and the like), polyvinylpyrrolidone, 2-pyrrolidone, polyacrylonitrile butadiene, polyamides, fluoropolymers (such as polytetrafluoroethylene and polyvinyl fluoride), a homopolymer and copolymers of styrene acrylonitrile, cellulose acetate, a homopolymer and copolymers of acrylonitrile butadiene styrene, polymethylpentene, polysulfones polyimides, polyisobutylene, polymethylstyrene and other similar compounds known to those skilled in the art.

Other materials of interest include any materials that can serve as filters for allergens, pollen, dander, smog, etc. By providing a filter within the device, sinusitis, sleep apnea, snoring, hay fever, allergic rhinitis, and other allergic respiratory conditions may be reduced or prevented. This filter may in fact be part of the airflow resistor or may be a separate component of the device. Any suitable filtering material known to those skilled in the art may be used with the respiratory devices described herein. Such materials include, but are not limited to, activated carbon charcoal filters, hollow-fiber filters, and the like.

In some versions, the respiratory device may comprise a filter that remains in the path of inhalation and/or exhalation during use. In some versions, the filter material remains in the path of both inspiratory and expiratory airflow. This filter material may not appreciably alter resistance to airflow in either direction, or it may alter airflow to substantially the same degree in both directions (inhalation and exhalation). In some versions, the filter comprises a material having a large pore size so that airflow is not significantly inhibited.

Operation of the Respiratory Device

The airflow resistor may be oriented in any direction. For example, in some embodiments of the device, the airflow resistor comprises valve flaps that are oriented such that both flaps are in a closed position during inspiration and in an open position during expiration. The respiratory devices may be orientated so that the airflow resistor increases resistance to expiration, and has a relatively lower or negligible resistance to inspiration. However, these devices can be oriented in the opposite direction as well, so that the device offers increased resistance to inspiration and decreased resistance to expiration. Such orientation may be used for a variety of pulmonary, cardiac, inflammatory, neurologic, or other disorders that might benefit from such changes in resistance and its subsequent changes to intra-thoracic and airway pressures. This version of the device may be structurally identical to other embodiments described elsewhere in this application. In some versions, the respiratory device is reversible, so that it may be used in either orientation by the user (e.g., to increase the resistance of inspiration relative to expiration in one orientation, or to increase the resistance of expiration relative to inspiration in another orientation). In some versions, the respiratory device is shaped so that the direction of the airflow resistor is immediately evident. For example, the respiratory device may be of a different shape or size on one end, or may include a visual indication. In one version, the respiratory device may be shaped so that it fits securely into a respiratory orifice only in one orientation (e.g., so that the airflow resistor inhibits the expiration more than it inhibits inhalation). For example, a flange or other mechanical stop may be used to insure proper orientation, while simultaneously preventing migration of the device further into the respiratory orifice.

In many embodiments, the device provides some level of resistance to expiration. It may be preferable to have little if any effect on resistance to inspiration, though in some cases, some degree of inspiratory restriction may be beneficial. In some versions of the device, both inspiration and expiration may be inhibited by the airflow resistor.

The device may also be adapted for comfort. Any device placed either in or around the oral cavity or in or around the nose should not be painful, and if possible not very noticeable by the patient. Thus, the holdfast may be shaped to conform to the attachment site in or around the respiratory orifice. In some versions, the holdfast comprises a flexible or shapeable material (e.g., a foam or other soft shape-memory material). In some versions, the entire respiratory device comprises a soft material.

Furthermore, the device may be adapted so that it is more or less visible to others. In some cases, the device may be configured to be placed high enough within the nostrils to make it difficult for others to see. Furthermore, the device may be of any color and/or pattern that help to camouflage it. In other versions, it may be useful to include colors and patterns that stand out, including ones that are fluorescent or otherwise offer increased visibility during the night or other setting where ambient light is reduced.

In some versions, the respiratory device may be "one size fits all", so that it may be used with any patient (or any patient of approximately the same size), despite differences in shapes and sizes of their nose/nostrils, oral cavity, teeth and other relevant anatomic features. In one version, the devices may conform to a range of sizes, for example "small," "medium," and "large" (or any other appropriate range, such as, e.g., a numerical range). Alternatively, the devices may involve a custom fit of the device or devices to the patient.

Custom fitting may improve patient comfort and potentially improve performance by improving the seal between the device and the patient's oral cavity, mouth, nasal cavity and nostrils, for example. In some versions, custom fitting may involve the placement of a device in warm or cold liquid or air with subsequent placement in the patient's nose or mouth. This process is meant to "prime" the materials in the device (e.g., particularly the materials of the holdfast), so that when holdfast is secured to the patient, the device permanently assumes a shape or configuration corresponding to a portion of the patients anatomy.

In some version of the devices described herein, an airflow resistor may fit within a larger structure (such as the passageway) so that some airflow through or around the airflow resistor is always allowed. For example, there might be a constant opening between the airflow resistor and the anchor that secures the airflow filter in communication with the passageway. This may ensure that expiratory and/or inspiratory airflow is never completely occluded. In some versions, the airflow resistor comprises a "hole" or opening. For example, a flap valve may comprise an opening through the flap valve permitting airflow through the flap valve even when the valve is closed.

The device may also create a PEEP effect by differentially changing the resistance to airflow in one direction based on the pressure applied against the device. For example, in some designs, expiratory airflow is subjected to resistance by the airflow resistor (or valve) until a certain threshold pressure differential or level of airflow is achieved; below that threshold, a more complete closure of the airflow resistor occurs (potentially completely occluding airflow through the device). The desired levels of PEEP are on the order of about 0.1 to about 30 cm $H_2O$ and more preferably about 1 to about 15 cm $H_2O$ pressure. Similarly, the differential resistance may also be triggered in the opposite direction; for example, above a certain threshold of pressure or level of airflow, the airflow resistor (e.g., valve) may open to decrease the resistance due to the airflow resistor, as when a patient coughs, sneezes, or blows his or her nose.

The optimal level of expiratory resistance or PEEP provided by the device may vary from patient to patient. In some versions, adequate expiratory resistance or PEEP is created to offer the desired benefits, but not providing too much expiratory resistance or PEEP so that the patient preferentially begins breathing through the mouth. In some cases, the user may test the device or devices while being monitored by a healthcare provider, a camera, a polysomnograph, or any other device that will help to assess the optimal level of resistance or therapy provided by the subject devices.

The use of an airflow resistor may also alter the inspiratory time:expiratory time ratio (I:E ratio), which is defined as the ratio of inspiratory time to expiratory time. The desired I:E ratio will be between about 3:1 and about 1:10 and more preferably about 1:1.5 to about 1:4 depending on the needs of the individual patient. In some versions, the desired ratio is approximately about 1:3.

In some versions, the device comprises an insertion, adjustment, or removal mechanism. In some cases, this mechanism involves any appropriate rigid or non-rigid positioner that facilitates removal or positioning of the device. Non-rigid positioners include but are not limited to cables, chains, wires, strings, chains, sutures, or the like. Rigid positioners include knobs, handles, projections, tabs, or the like. A user may grasp or otherwise manipulate the positioner to facilitate insertion, re-adjustment, or removal of the device. Furthermore, various applicators or other insertion devices may be used. For example, a tubular applicator holding a respiratory device adapted for insertion into a nasal cavity may be advanced into the nasal respiratory orifice (e.g., nostril) to insert the respiratory device.

In some cases, the device may be oversized. Oversizing the device may reduce resistance in one or more direction of airflow. In some versions, the passageway through the device is oversized. In some versions, an outer portion of the device that contacts the respiratory orifice is oversized. Thus, the respiratory device may exert pressure against the nasal cavity of a user. In patients with obstructive sleep apnea or snoring, for example, increasing the size of the a respiratory device configured to be inserted into one or more nostrils may prevent the more distal tissues of the airway, tongue, and nasopharynx from being sucked in or closed during inspiration. Moreover, airflow through an oversized passageway may assume a less turbulent flow profile, resulting in a decreased propensity for noise production in the case of snoring, for example. Similarly, the respiratory device passageway may be shaped so as to decrease turbulence of airflow. Likewise, the shape and activity of the airflow resistor may be chosen to minimize turbulence and, therefore, sound or vibration.

In some versions, the device is used with an active agent. In some versions, the active agent comprises a drug. An active agent (e.g., a medicament) or other compound can be placed in or on the device to deliver the active agent into the mouth, tongue, hard and soft palates, sinuses, nose, pharynx, vocal cords, larynx, airways, lungs, trachea, bronchi, bronchioles, alveoli, air sacs, or any tissues that are exposed to inspiratory or expiratory airflow. In some cases, the active agent may be embedded or impregnated in the device or components of the device. In some cases the active agent is a coating. An active agent may comprise any compound that is in some way useful or desirable for the patient. For example, the active agent may be any odorant, including: menthol, phenol, eucalyptus, or any agent that provides a fragrance in the inspired air. Alternatively, an active agent may comprise a drug with beneficial effects, such as beneficial vasculature effects. For example, an active agent may comprise a drug that effects the blood vessels (oxymetazoline or any other vasoactive compound), nasopharynx, airways or lungs (albuterol, steroids, or other bronchoconstriction or bronchodilation compounds). An active agent may comprise an antibiotic or a steroid for example. The above list of active agents is not meant to be limiting.

An active agent may be placed in or on any portion of the device. Furthermore, the location of the active agent within the respiratory device may specifically guide the delivery of the active agent. For example, in versions of the respiratory device configured to be placed inside a respiratory cavity, when the holdfast comprises an active agent (e.g., coated, embedded or otherwise part of the holdfast), the drug may be delivered through the mucus membranes of the respiratory cavity. In another example, an active agent may be included as a powder or releasable coating that may be aerosolized and delivered within the respiratory system. Thus, an active agent may be on a surface of the device (e.g., the passageway, holdfast or airflow resistor) or embedded within any surface of the device. A separate drug-containing region may also be included in the device. The addition of an active agent may be of particular interest in treating allergies and sinusitis. Respiratory devices (with or without airflow resistors) may therefore comprise active agents such as menthol or other fragrant compounds.

In some versions of the devices, an airflow resistor is not present. The device may comprise a passageway and a holdfast and may or may not include additional support such as a rim. In some cases, the holdfast may be of adequate strength to support and prevent migration or movement of the device, and to provide adequate radial support to prevent reduction of the passageway of the device during the various phases of the respiratory cycle. In this case, the device props open the nasal or oral cavities to facilitate inspiratory and/or expiratory airflow. This may be helpful in preventing obstructive sleep apnea and snoring since these disorders can be treated, for example, by increasing the size of the nares. This is partly due to the tendency of the nares and nasal cavity to collapse due to negative inspiratory pressures. Thus, preventing these nasal tissues from collapsing may prevent further downstream tissues in the nasopharynx from collapsing. As mentioned earlier, the device may be oversized relative to the size of the nares or nasal cavity in order to reduce resistance and maximize airflow.

The respiratory devices may be manufactured and assembled using any appropriate method. Representative manufacturing methods that may be employed include machining, extruding, stamping, and the like. Assembling methods may include press-fitting, gluing, welding, heat-forming, and the like.

Turning now to the figures, FIG. 1 provides a perspective view of one version of the respiratory device 1 in which the device can fit into the oral cavity of a user. The holdfast 5 comprises grooves 2 and 3 in which the user's teeth and/or gums may preferentially sit, thus securing the device in the oral cavity. Airflow resistor 4 represents any airflow resistor capable of modulating inspiratory and/or expiratory resistance during any or all portions of the respiratory cycle, as described above. The airflow resistor 4 sits within a passageway 6.

Figure 2:
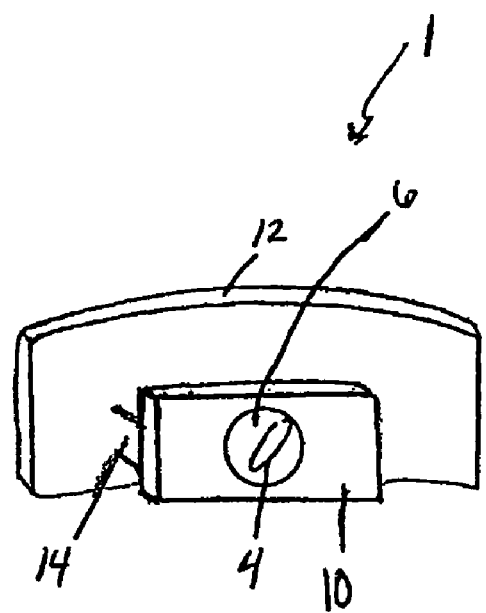
FIG. 2 is a perspective view of another respiratory device adapted for the oral cavity.

FIG. 2 is a perspective view of another embodiment of the respiratory device 1 that may be fitted in an oral cavity. In this embodiment, the patient's teeth and/or gums help to secure the device in place by contacting the holdfast. The holdfast comprises an inner frame 10, and outer frame 12, and a positioner 14. The inner frame 10 is located on the internal portions of the patient's teeth or gums. The outer frame 12 is positioned outside the patient's teeth/gums or outside the patient's lips. The positioner 14 is located between the upper and lower jaws, teeth, and/or gums. An airflow resistor 4 modulates inspiratory and/or expiratory resistance during any or all portions of the respiratory cycle.

Figure 3:
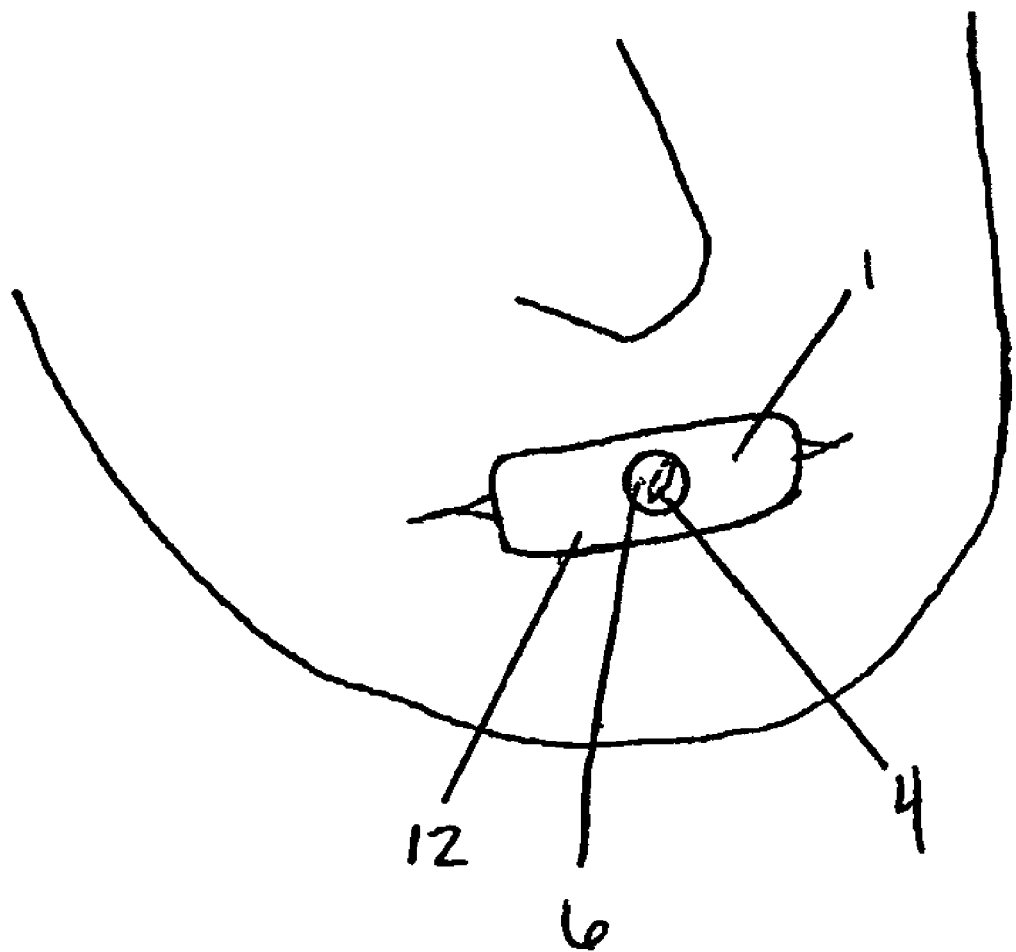
FIG. 3 is a perspective view of the device shown in FIG. 2, where the device is positioned in a patient's oral cavity.

FIG. 3 is a view of the device 1 shown in FIG. 2, where the device is depicted within and protruding from the patient's oral cavity. The outer frame 12 of the holdfast is shown outside of the patient's teeth and gums. The airflow modulator 4 within the passageway 6, modulates inspiratory and/or expiratory resistance during any or all portions of the respiratory cycle through the oral respiratory passageway. One or more airflow resistors 4 and/or passageways 6 may be used in this (or any, e.g., oral or nasal) respiratory device.

Figure 4:
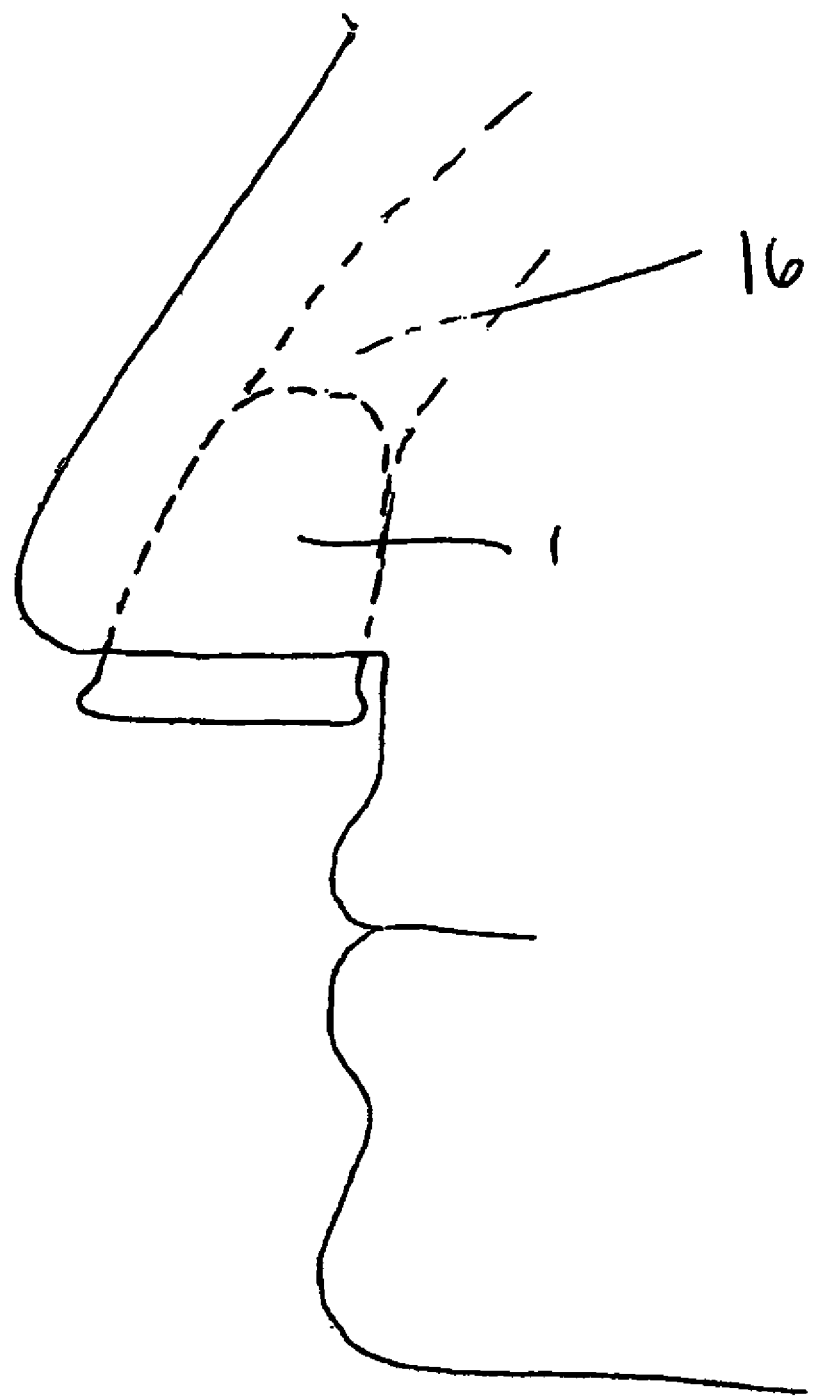
FIG. 4 shows a respiratory device adapted for the nasal cavity.

FIG. 4 is a perspective view of another embodiment of the respiratory device 1 in which the device is removable and may be secured within a patient's nasal cavity 16. In this embodiment, the device protrudes from the nasal opening. The sides of the device comprise a holdfast which is shown fitting snugly within the nasal passage, as well as projecting out from the nasal passage.

Figure 5:
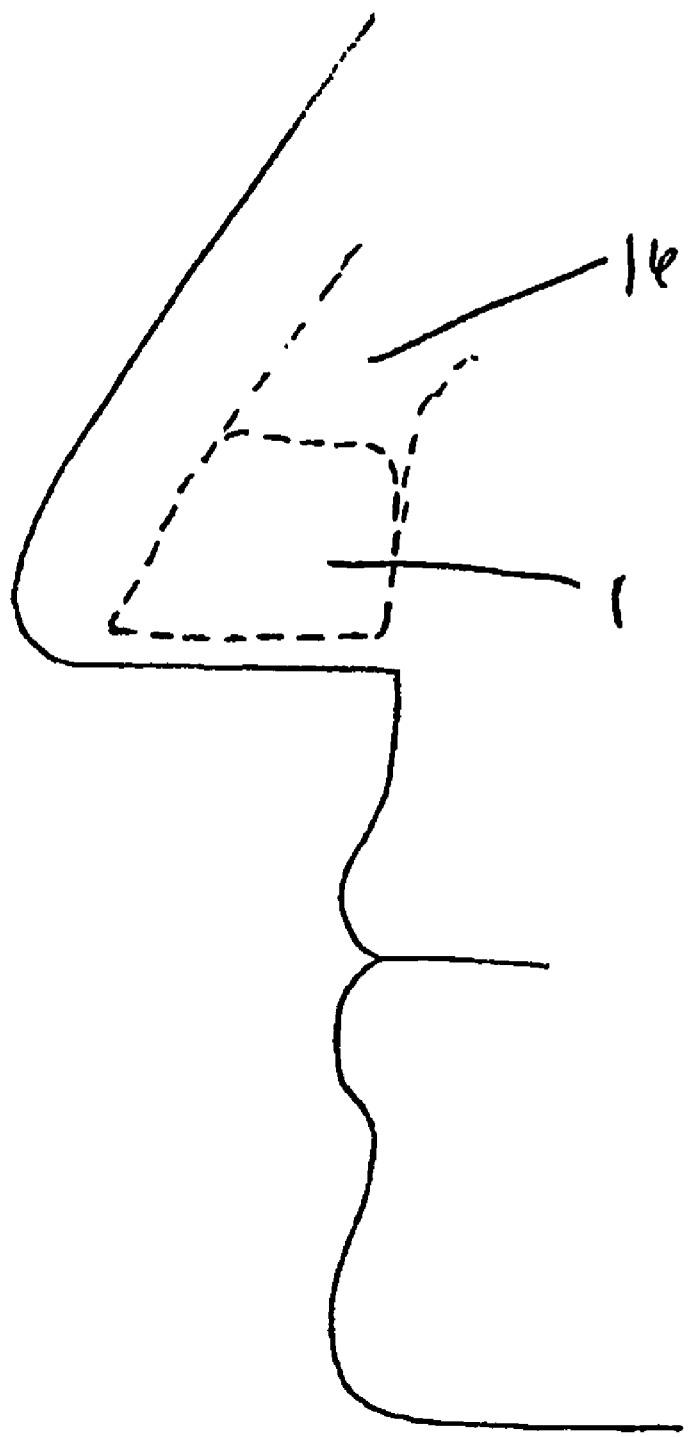
FIG. 5 shows a respiratory device adapted to fit substantially within the nasal cavity.

FIG. 5 is a perspective view of another version of the respiratory device 1 in which the device is placed completely within the nasal passage 16. The entire respiratory device fits snugly within the nasal passage.

Figure 6:
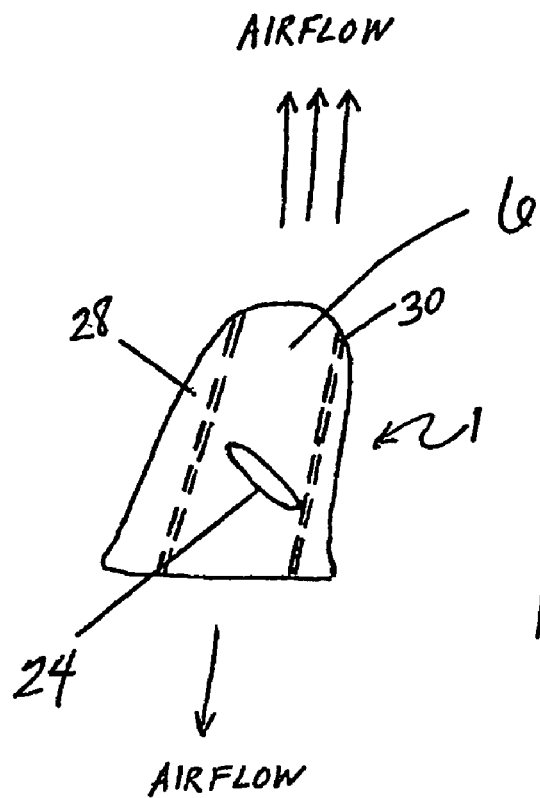
FIG. 6 shows a cross-sectional view of the device shown in FIG. 4, where an airflow resistor is shown within the device.

FIG. 6 is a cross-sectional view of a respiratory device 1 similar to those shown in FIGS. 4 and 5. A holdfast 28 comprises the outer surface of the device that contacts the inner portions of the nasal cavity, thus serving to secure the device in place while ideally creating a partial or complete seal. The passageway 6 through which air may flow is surrounded by a rim 30 that provides additional structural support to the device. A rim 30 is not required, particularly if the walls of the passageway (which may be defined by the holdfast 28, for example) provide sufficient support. An airflow resistor 24 is included within the passageway which may modify inspiratory and/or expiratory resistance during any or all portions of the respiratory cycle.

Figure 7A:
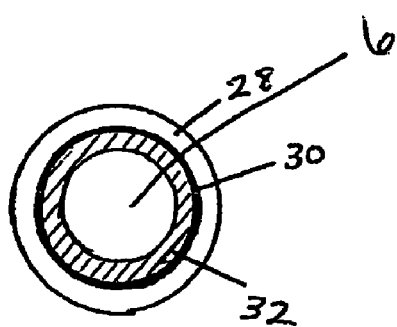
FIGS. 7a and 7b show cross-sectional views of the device shown in FIG. 4.
Figure 7B:
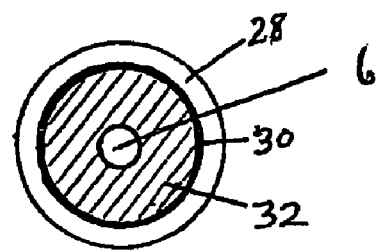

FIGS. 7a and 7b show more detailed views of the operation of airflow resistors shown in FIGS. 4 and 5. These cross-sectional views illustrate the holdfast 28, the optional rim 30, the passageway 6, and the airflow resistor, shown as a valve 32. The rim 30 separates the holdfast 28 and the valve 32, frames the valve 32, and provides overall structural support to the entire device. In FIG. 7a, the valve 32 is shown in the open position, providing less resistance to airflow. In FIG. 7b, valve 32 is shown in the closed position, providing more resistance to airflow, because the cross-sectional area of the passageway 6 has been constricted by the closing of the valve.

Figure 8A:
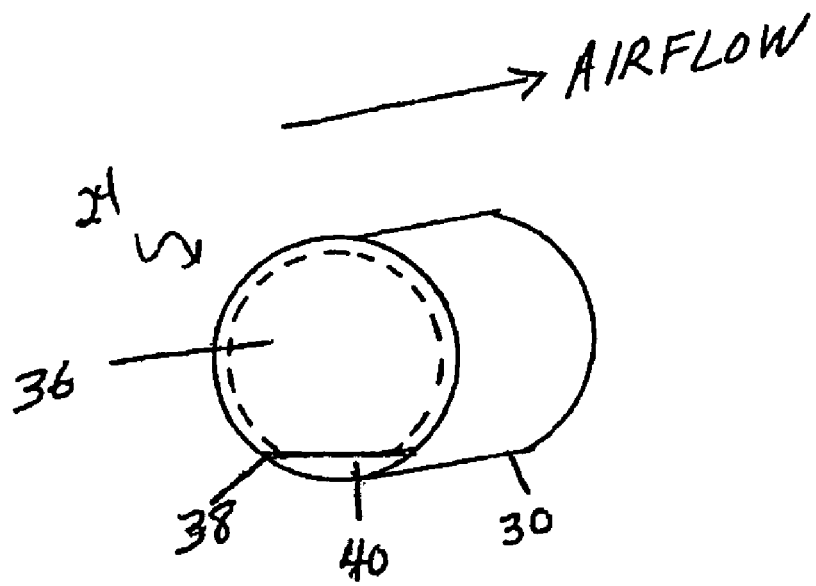
FIGS. 8a and 8b are perspective views of a respiratory device showing an airflow resistor during exhalation (FIG. 8a) and inhalation (FIG. 8b), respectively.
Figure 8B:
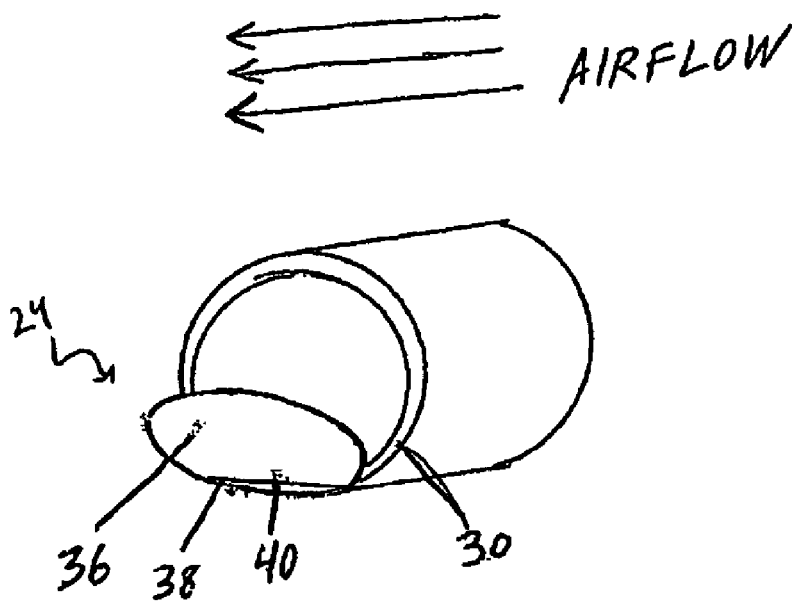

FIGS. 8a and 8b show perspective views of an airflow resistor that could be used, for example with any of the devices described in FIGS. 1-5. In these figures, a rim 30 is shown. The rim may be part of the holdfast which positions and secures the device within a respiratory passageway; alternatively, additional material (e.g., compliant material) may be attached to the rim to form the holdfast. In FIGS. 8a and 8b, the rim provides support to the airflow resistor 24. The airflow resistor is shown here as a flap valve mechanism that comprises a flap 36 that pivots around a joint 38 and is connected to a fixed element 40. Fixed element 40 is attached to the inner region of the passageway 6, which is defined in this figure by the rim 30. In some versions, the flap valve and the inner surface of the passageway 6 (e.g., the rim 30) may constitute a single piece. Alternatively, the flap 36, joint 38, and fixed element 40 may be fabricated as a single piece, in which case joint 38 may be a hinge. Thus, joint 38 may be a pinned hinge or a non-pinned hinge joint. Alternatively, rim 30, flap 36, joint 38, and fixed element 40 may all be created as a single piece or material. Thus, flap 36 is able to pivot in relation to fixed element 40 depending on the direction of the patient's airflow and the desired level of resistance to airflow. FIG. 8a shows the airflow resistor with flap 36 in a closed position during expiration, thus providing increased resistance. In some versions, the flap portion of the airflow resistor closes completely, as shown. In these versions, the edges of the flap 36 may close off the entire passageway (as shown), or may only occlude a portion of the passageway. FIG. 8b shows the airflow resistor with flap 36 in the open position (e.g., during inspiration), thus providing decreased resistance. Flap 36 may define a hole, or may have other openings (which may stay open during all or part of the respiratory cycle) to help modulate the degree of inspiratory and expiratory resistance. The flap 36 may return to a preferred opened or closed position. For example, a shape memory material, a spring (such as a torsion spring), or the holdfast may apply force to flap 36 to return it to a closed position. For example, the use of foam or urethane surrounding the airflow resistor may provide such force as to close flap 36 in the absence of adequate airflow. Bi-leaflet versions of the airflow resistor are also contemplated and will have similar function. These bi-leaflet versions may involve multiple sets of flaps 36, joints 38, and fixed elements 40, etc.

Figure 9A:
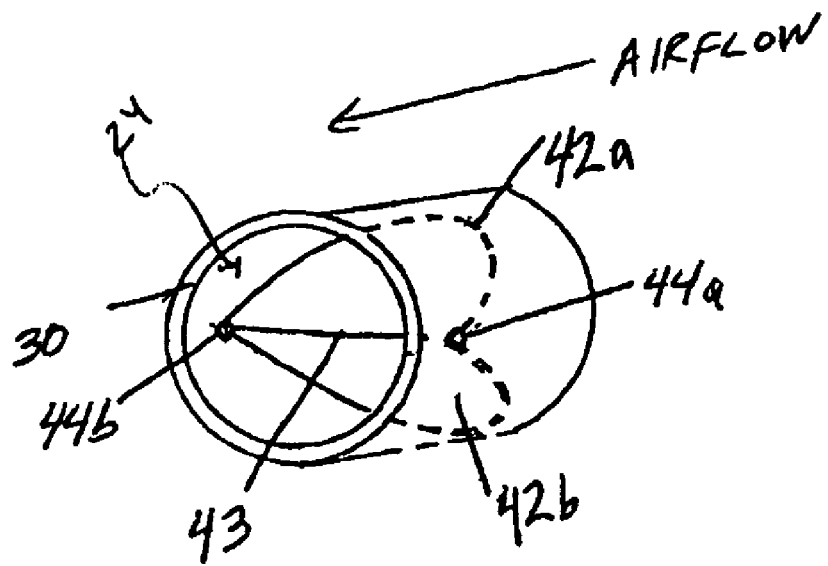
FIGS. 9a and 9b are perspective views of a respiratory device having an airflow resistor where the airflow resistor is shown during exhalation (FIG. 9a) and inhalation (FIG. 9b), respectively.
Figure 9B:
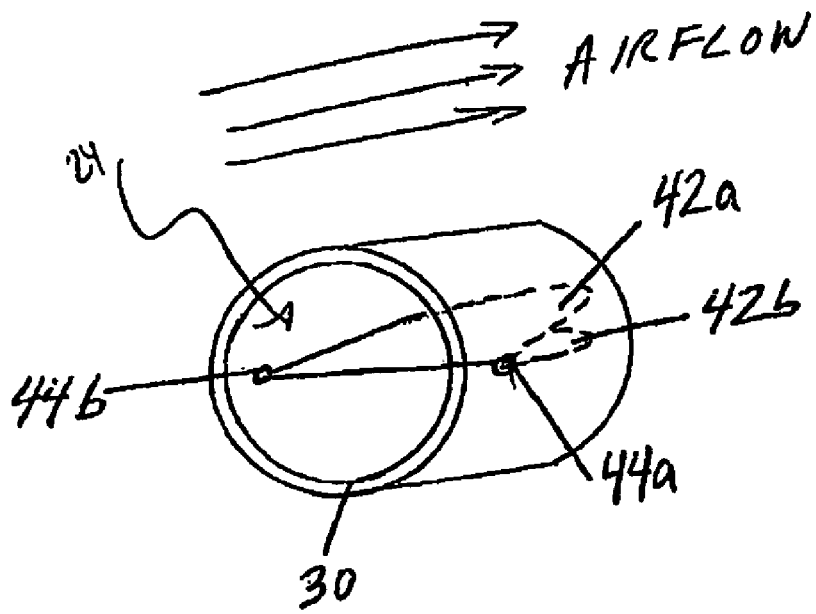

FIGS. 9a and 9b show a perspective view of another embodiment of an airflow resistor that could be used in any of the respiratory devices described herein. The inner surface of the passageway shown includes a rim 30 that supports the airflow resistor. This airflow resistor 24 is also shown as a valve mechanism. Moveable elements 42a and/or 42b (flaps) are attached to one another or are constructed from a single piece. Moveable elements 42a and 42b are attached to the inner surface of the passageway (shown as a rim 30) at attachment points 44a and 44b, and these attachment points may allow the valve to pivot around a hinge 43 in response to direction and amplitude of airflow. In one version, attachment points 44a and 44b are formed directly into the rim 30 or holdfast 28 during the manufacturing (e.g., casting) process. In one version, the hinge is statically attached to an inner region of the passageway, and the flaps 42a and 42b are movably (or flexibly) attached to the hinge. FIG. 9a shows this airflow resistor when the resistance is high (e.g., the flap valve is mostly closed), as during expiration, and FIG. 9b shows the airflow resistor when the resistance is low (e.g., the flap valve is mostly open), as during inspiration.

Figure 10:
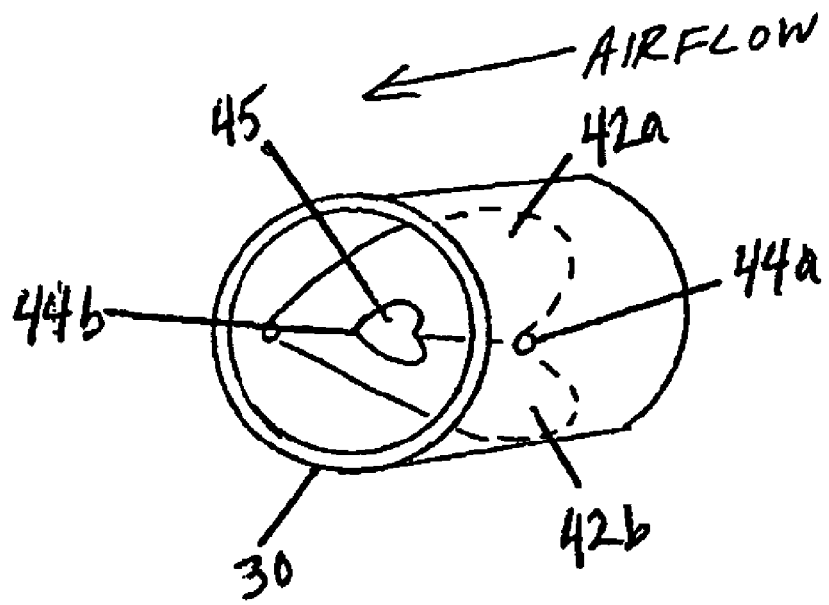
FIG. 10 is a perspective view of a respiratory device having an airflow resistor where the airflow resistor is shown during exhalation.

FIG. 10 shows a perspective view of another embodiment of an airflow resistor that is similar in structure and function to the device shown in FIGS. 9a and 9b. However, the airflow resistor shown has an internal opening 45 that is located approximately where moveable elements 42a and 42b pivot relative to one another. The addition of internal opening 45 modulates airflow (e.g., inspiratory or expiratory airflow) by altering the level of resistance. Addition of this opening reduces the resistance in one direction (e.g., expiratory resistance, when the flap valve is "closed") more than resistance in the opposite direction (e.g., inspiratory resistance, when the flap valve is "open").

Figure 11:
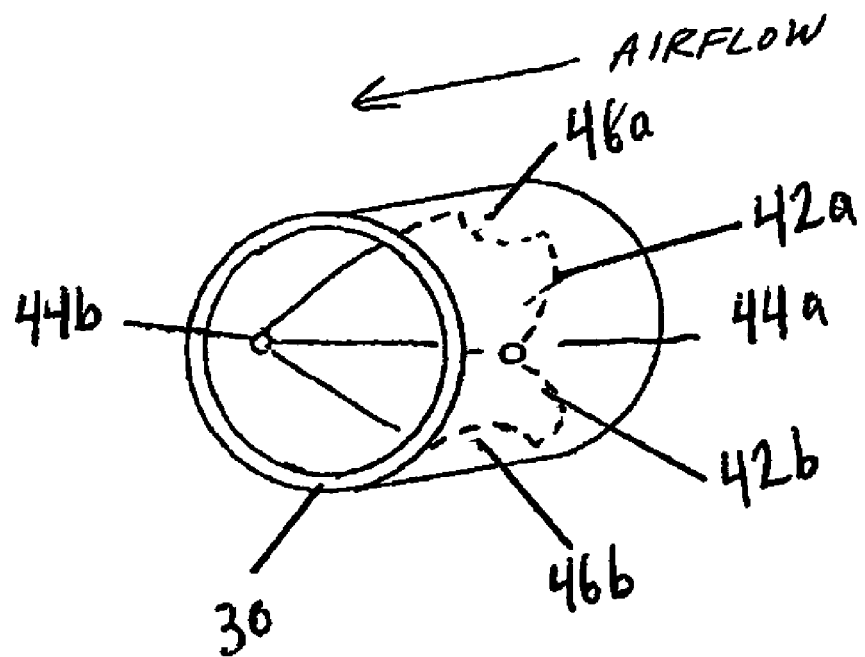
FIG. 11 is a perspective view of a respiratory device having an airflow resistor where the airflow resistor is shown during exhalation.

FIG. 11 shows a perspective view of another embodiment of an airflow resistor that is similar in structure and function to the device shown in FIGS. 9a and 9b. Peripheral openings 46a and 46b are placed completely within, or on the periphery of the moveable elements 42a and 42b. These peripheral openings 46a and 46b also modulate inspiratory and/or expiratory resistance. The addition of peripheral openings 46a and 46b helps modulate inspiratory and expiratory airflow by altering the level of resistance. Addition of these peripheral openings also reduce the resistance in one direction (e.g., expiratory resistance, when the flap valve is "closed") more than resistance in the opposite direction (e.g., inspiratory resistance, when the flap valve is "open").

Figure 12A:
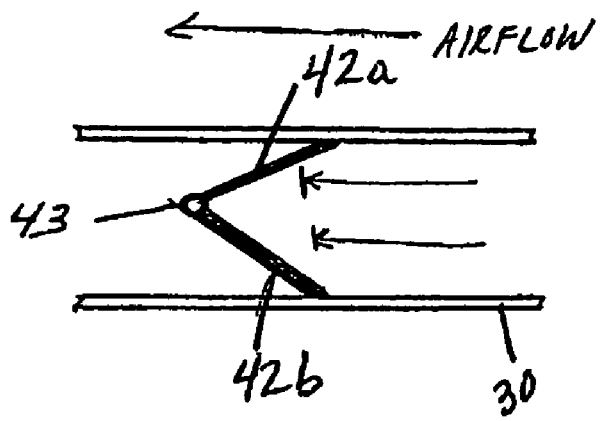
FIGS. 12a and 12b show cross-sectional views of the respiratory devices shown in FIGS. 9a, 9b, 10, and 11 during exhalation (FIG. 12a) and inhalation (FIG. 12b), respectively.
Figure 12B:
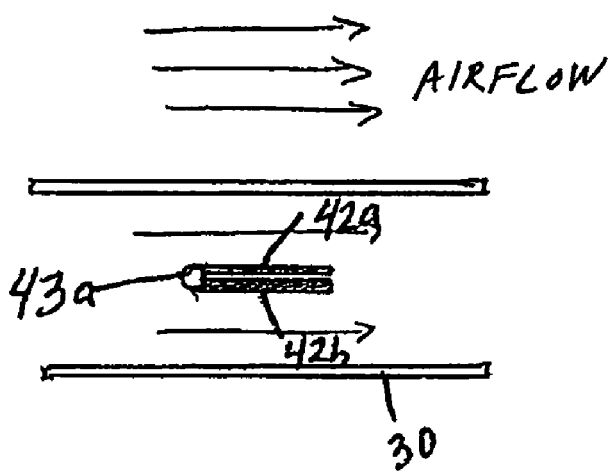
Figure 12C:
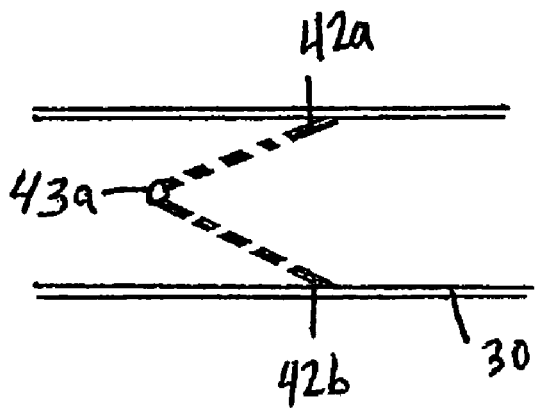
FIG. 12c shows a cross-sectional view of a variation of the respiratory device during exhalation.

FIGS. 12a and 12b show more detailed views of the operation of the valve mechanisms as described in FIGS. 9a, 9b, 10, and 11. In this figure, we assume that the airflow resistor is oriented so that the airflow resistor increases resistance during expiration relative to inhalation (e.g., the lungs are located to the right in FIGS. 12a, 12b and 12c). Moveable elements 42a and 42b are coupled to each other via hinge 43. FIG. 12a demonstrates the valve mechanism during expiration, in which moveable elements 42a and 42b are in a closed position due to the expiratory airflow in the direction from the lungs to the external environment. FIG. 12b demonstrates the valve mechanism during inspiration, in which moveable elements 42a and 42b are in an open position due to the inspiratory airflow in the direction from the external environment to the lungs. FIG. 12c demonstrates a modification of the valve mechanism shown in FIGS. 12a and 12b in which there are one or more apertures within or on the periphery of the moveable elements that reduce resistance to expiratory airflow, further increasing the rate of expiratory airflow. All of these valve mechanisms and configurations can be placed in the opposite orientation so that inspiratory airflow leads to valve closure and expiration leads to valve opening.

Moveable elements (flaps) 42a and 42b of the airflow resistor may be made of any appropriate material. In particular, materials which have sufficient stiffness to withstand the forces applied by the respiratory process. Furthermore, durable materials (e.g., which may withstand the moisture, etc. of the respiratory passage) may also be desirable. In some versions, the devices are disposable, and thus durability may be less critical. Furthermore, the moveable elements 42a and 42b may also be made from porous materials or filters, etc. that do not overly restrict or resist airflow but at the same time can remove debris, pollen, allergens, and infectious agents for example.

Figure 13A:
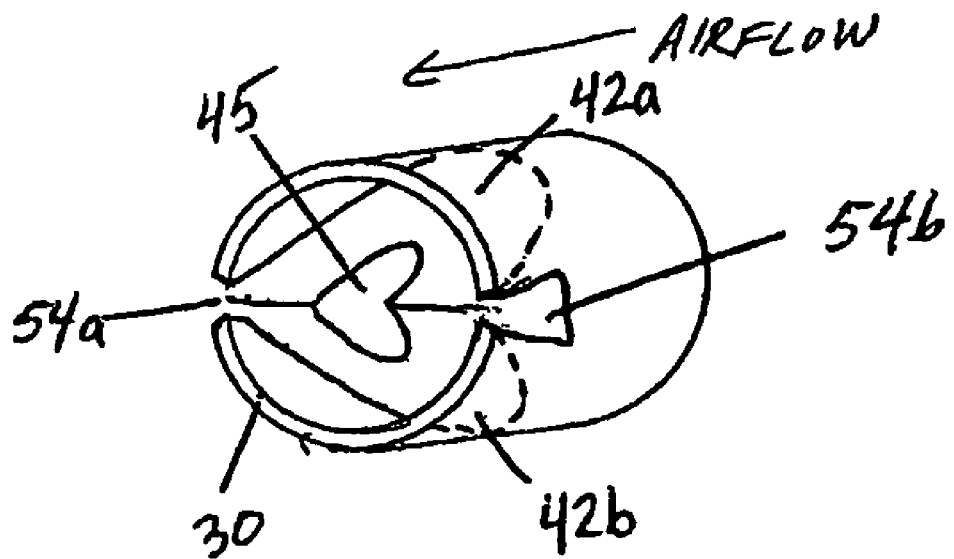
FIGS. 13a and 13b are perspective views of a respiratory device having an airflow resistor where the airflow resistor is shown during exhalation (FIG. 13a) and inhalation (FIG. 13b), respectively.
Figure 13B:
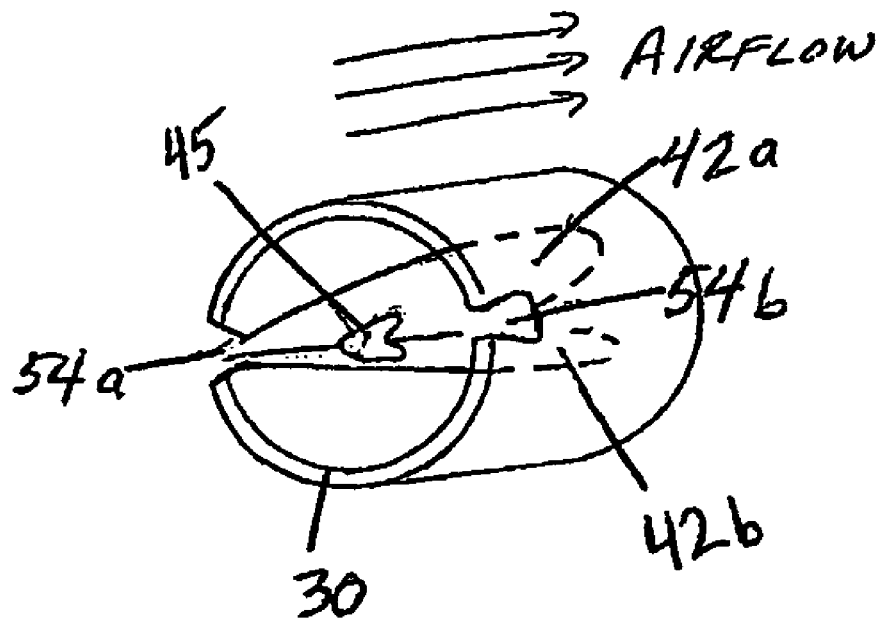

FIGS. 13a and 13b show perspective views of another airflow resistor that could be used in any of the devices described herein. FIG. 13a shows the airflow resistor (a flap valve) in a closed position, as might be seen during expiration, resulting in increased resistance to airflow. FIG. 13b shows the airflow resistor in an open position, as might be seen during inspiration, resulting in a decreased resistance to airflow relative to the closed position. Because of the small profile of the retracted flap valves, the resistance added by the airflow resistor when the airflow resistor is "open" may be negligible. Moveable elements 42a and 42b are attached to each other or are a single piece. Moveable elements 42a and 42b are attached to the walls of the passageway (in this example, defined by a rim 30), to the rim 30, or to the holdfast 28 by a securing element 54a and 54b which uses a tab, adhesives, press fit, external pressure (as from a holdfast 28) or any way known to those skilled in the art. Internal opening 45 is located centrally, decreasing the resistance to expiratory airflow (in the "closed" state), although peripheral locations are also contemplated. In some versions, the size and number of openings in the valves may determine the resistance of the airflow resistor. Thus, the size and number of openings may be selected in order to determine the I:E ratio.

Figure 14:
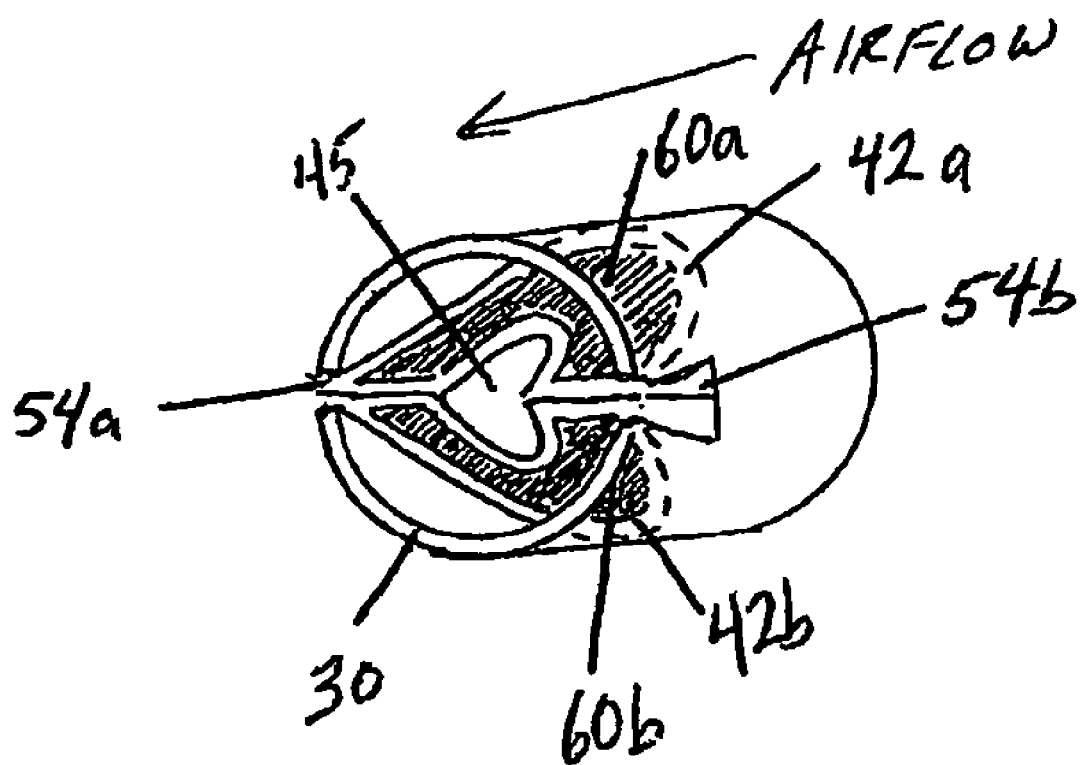
FIG. 14 is a perspective view of a respiratory device having an airflow resistor where the airflow resistor is shown during exhalation.

FIG. 14 provides a perspective view of another embodiment of an airflow resistor that is similar in structure and function to the airflow resistor shown in FIGS. 13a and b. In FIG. 14, the movable elements further comprise a reinforcement support 60a and 60b that is located partially or completely covering the moveable elements 42a and 42b. The reinforcement support provides additional structure and/or support to these moveable elements. Furthermore, reinforcement support 60a and 60b may also promote a more reliable seal and may standardize the movements of moveable elements 42a and 42b while reducing the likelihood that moveable elements will invert, buckle in the direction of airflow, or otherwise fail, especially when exposed to high pressures and airflow as might be seen during coughing. The addition of reinforcement support 60a and 60b also dampens any whistling or other sounds during inspiration or expiration. Moveable element 42a and reinforcement support 60a and moveable element 42b and reinforcement support 60b may be a single unit (or each "flap" may be a single unit). Alternatively, both moveable elements 42a and 42b and both reinforcement support 60a and 60b may be a single unit. A central opening 45 is also shown in the figure.

Figure 15A:
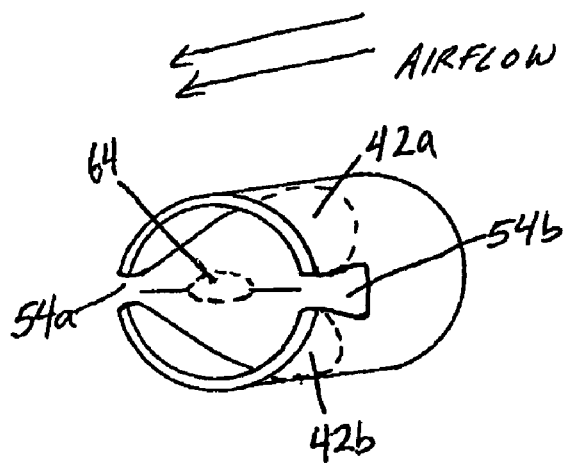
FIGS. 15a, 15b, and 15c are perspective views of a respiratory device having an airflow resistor.
Figure 15B:
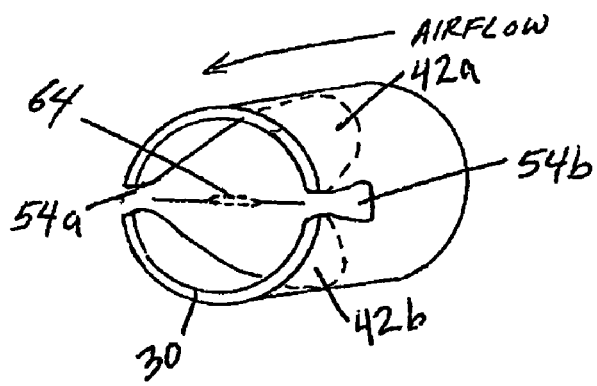
Figure 15C:
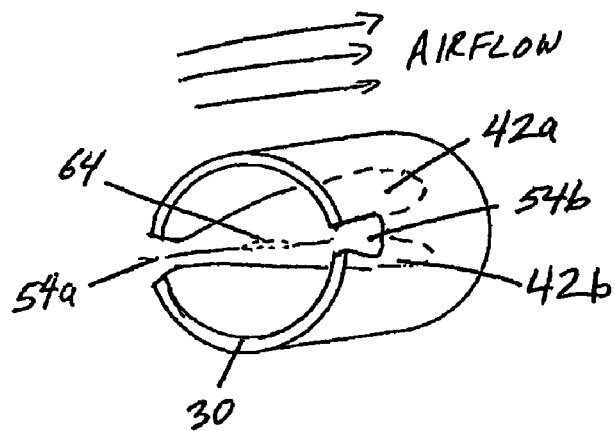

FIGS. 15a-15c show perspective views of another embodiment of an airflow resistor that may be used in any of the devices described herein. The airflow resistor is similar to that shown in FIGS. 13a and 13b with the exception that internal opening 45 is replaced by another airflow resistor 64 (a "nested airflow resistor"). This nested airflow resistor 64 automatically closes when the flow through the valve (or the pressure differential across the valve) falls below a predetermined level. This allows the airflow resistor (with the nested airflow resistor region) to provide positive end expiratory pressure (PEEP). In FIG. 15a, the airflow resistor is shown during exhalation, and the moveable elements 42a and 42b of the airflow resistor are in the closed position. The nested portion of the airflow resistor 64 is open so long as the pressure differential across the airflow resistor and/or airflow is above a certain level. Thus, this figure demonstrates the beginning of expiration, when airflow in the passageway and pressure differential are largest. In FIG. 15b, the same airflow resistor is again shown during expiration, and moveable elements 42a and 42b of the airflow resistor are still in the closed position. However, the nested airflow resistor region 64 now assumes a closed position, since the pressure differential across the airflow resistor and airflow through the passageway is no longer above the threshold value. This scenario may correspond to the later stages of exhalation, when airflow and pressure differential are decreasing or are lower. Thus, at the end of exhalation, PEEP has been created. For example, the nested airflow resistor 64 may be set to close whenever air pressure in the respiratory orifice coming from the lungs is less than 5.0 cm $H_2O$. FIG. 15c shows the device during inhalation, in which moveable elements 42a and 42b of the airflow resistor are in the open positions, allowing inhalatory airflow with minimal resistance to said airflow.

Figure 16A:
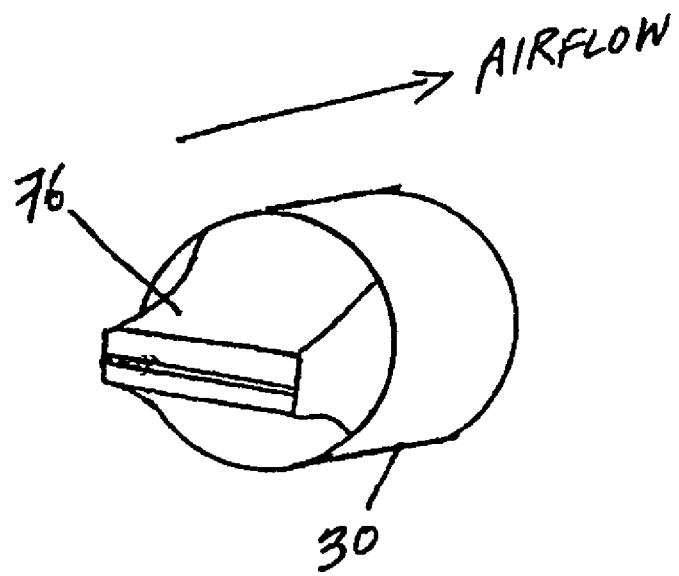
FIGS. 16a and 16b are perspective views of a respiratory device having an airflow resistor where the airflow resistor is shown during exhalation (FIG. 16a) and inhalation (FIG. 16b), respectively
Figure 16B:
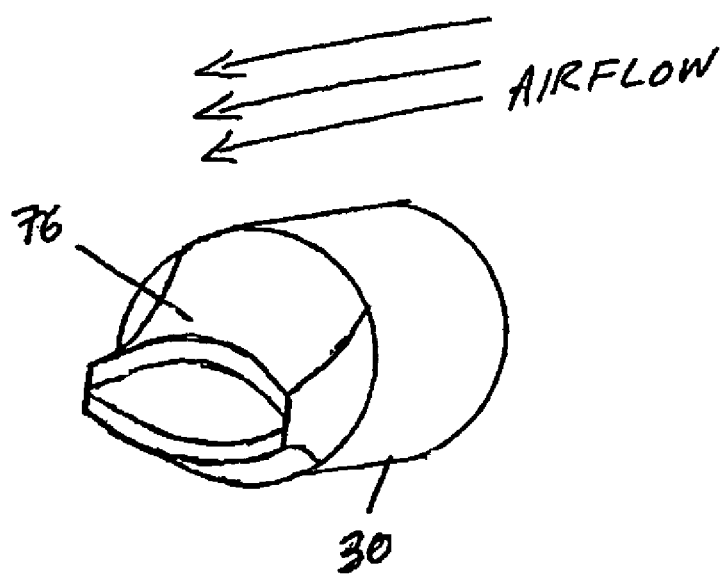

FIGS. 16a and 16b show perspective views of another embodiment of an airflow resistor that may be used in any of the devices described herein. FIG. 16a shows a hingeless valve 76 in a closed position during exhalation, in which there is increased resistance to airflow. FIG. 16b shows a hingeless valve 76 in an open position during inspiration, in which there is decreased resistance to airflow. The hingeless valve 76 may also comprise one or more holes within its structure to allow airflow in either direction at various stages of the respiratory cycle. For example, despite being in a closed position, the hingeless valve 76 would still allow some level of expiratory airflow. Alternatively, the hingeless valve 76 might never close completely. Even in a closed state, its flaps may never completely block all airflow.

FIGS. 17a and 17b show perspective views of another embodiment of an airflow resistor that could be used in any of the devices described herein. The membrane-type airflow resistor show in FIGS. 17a and 17b comprises a membrane 80 (that may or may not be floppy) that is attached by a connector 82 to the body of the airflow resistor. During exhalation, shown in FIG. 17a, the membrane 80 seats itself against a rim 30 and/or an apposition support 84 which may project from the sides of the passageway (e.g., from the rim 30) to support the membrane 80 during exhalation. FIG. 17b shows the situation during inhalation, when the membrane 80 in a deflected position, thereby decreasing resistance to inspiratory airflow, and increasing airflow through the airflow resistor. Membrane 80 may have an opening 86 (or openings) which remain open during both inspiration and exhalation. In some versions of the airflow resistor, membrane 80 does not have an opening. In still other versions, there are several openings within membrane 80.

FIGS. 18a and 18b show cross-sectional views of another embodiment of an airflow resistor that could be used in any of the devices described herein. FIG. 18a shows the airflow resistor during inspiration, during which deformable member 90 is unfurled leading to decreased resistance and increased airflow. FIG. 18b shows the airflow resistor during expiration, during which deformable member 90 assumes an orientation or folding configuration that leads to increased resistance and decreased airflow. Deformable member 90 may have a preferred default position (a tendency to default to a preferred orientation in the absence of external influences or pressures) that may allow such an airflow resistor to offer a PEEP effect.

Figure 19A:
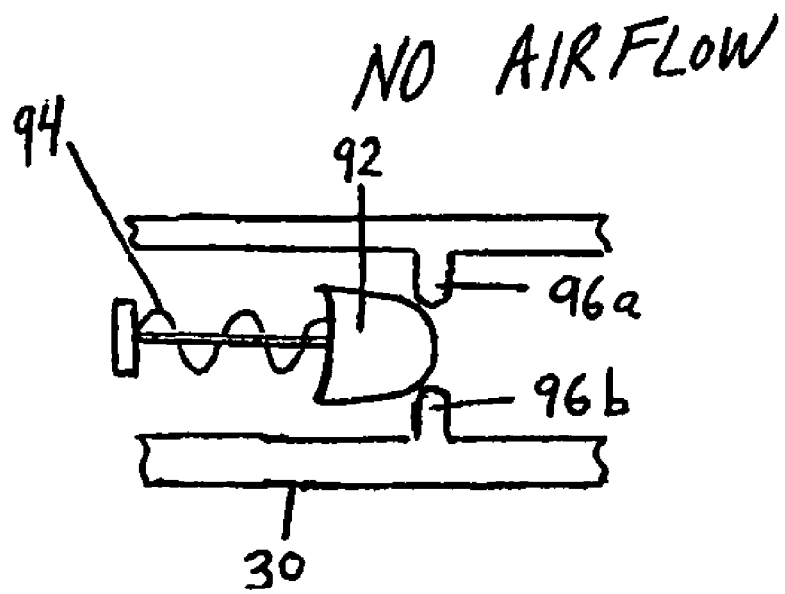
FIGS. 19a and 19b are cross-sectional views of a respiratory device having an airflow resistor where the airflow resistor is shown during low pressure and/or low airflow exhalation (FIG. 19a), and then during high pressure and/or high airflow exhalation (FIG. 19b).
Figure 19B:
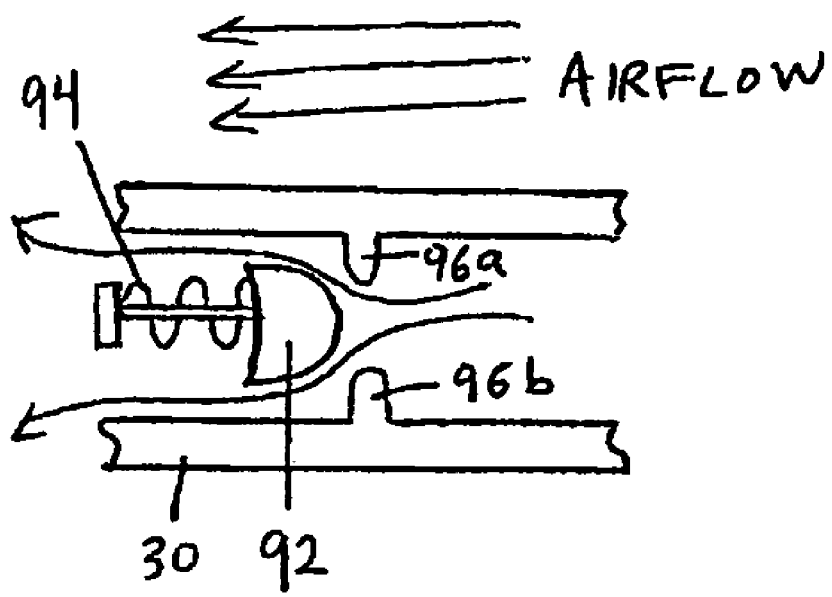

FIGS. 19a and 19b show cross-sectional views of another embodiment of an airflow resistor that could be used in any of the devices described herein. This is a stopper-type airflow resistor. FIG. 19a shows the airflow resistor on exhalation with little to no airflow and minimal pressure differential across the valve. FIG. 19b shows the device during more robust exhalation, characterized by increased airflow and increased pressure differential across the valve. Stopper 92 is connected to return mechanism 94. Stopper 92 may also have an opening within it to allow airflow at all times or at specific parts of the respiratory cycle (e.g., another, nested, airflow resistor, such as one allowing airflow during inhalation, but not exhalation), thereby providing fluid communication between the airways and the external environment. Alternatively, stopper 92 may have a valve portion that is open during inhalation and closed during exhalation, or vice verse. In FIG. 19a, the airflow from right to left is insufficient to overcome the spring force provided by return mechanism 94, and stopper 92 seals against seating supports 96a and 96b. In FIG. 19b, the airflow from right to left is sufficient to overcome the spring force provided by return mechanism 94, and stopper 92 is displaced leftward and thus expiratory airflow is allowed. The mechanism described in FIGS. 19a and 19b is one way in which PEEP can be created by the device.

Figure 20:
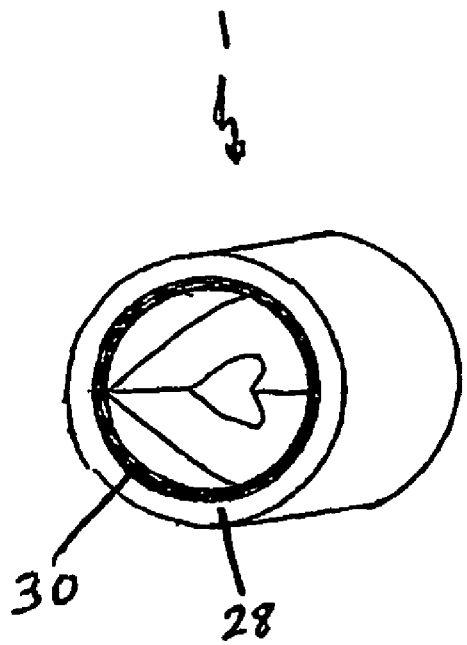
FIG. 20 is a perspective view of a respiratory device where the device is removable and adapted for the nasal cavity.

FIG. 20 is a perspective view of another embodiment of the respiratory device where the device is removable and may be placed in communication with the nasal cavity. In FIG. 20, a holdfast 28 is located between the patient's nose and the airflow resistor in the device 1, providing a partial or complete seal, anchoring the device, and providing comfort for the patient. The holdfast 28 has a cross section that is roughly circular and capable of fitting within a patient's nostrils.

Figure 21:
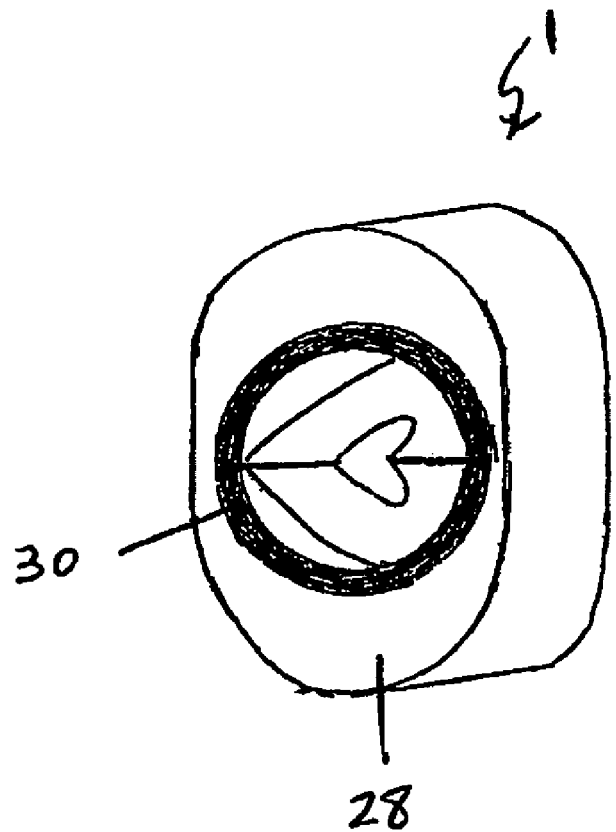
FIG. 21 is a perspective view of a respiratory device where the device is removable and adapted for the nasal cavity.

FIG. 21 is a perspective view of another embodiment of a respiratory device where the device is removable and may be placed within the nasal opening. This device shows a holdfast 28 having an approximately oval cross-section. Many such cross-sectional shapes are possible to optimize placement, anchoring, sealing, and comfort, including a variety of conical or asymmetric shapes designed to fit within a patient's nasal openings. In some cases, the rim 30 and/or any airflow resistor 4 may also assume any desired cross sectional shape, including that of an oval or any other non-circular orientation. In some embodiments, the holdfast 28 will be shapeable, deformable, or adjustable by the patient either before, after, or during placement of the device. Alternatively, the device can be customizable to fit individual patients through the use of imaging modalities including MRI, CT, xray, or direct vision, or through the use of molding techniques that are common in dentistry and other fields.

Figure 22:
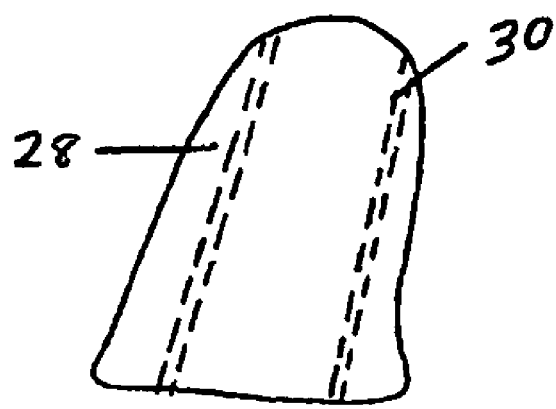
FIG. 22 is a cross-sectional view of a respiratory device where the device is removable and adapted for the nasal cavity.

FIG. 22 is a cross-sectional view of an embodiment of a respiratory device where the device is removable and may be secured in fluid communication with a nasal cavity. In this version, the device does not contain any moveable components that alter airflow. The device comprises a holdfast 28 and rim 30 that lends the device support. The device may be oversized to decrease resistance and increase airflow in one or more directions. In some cases, a drug (with either an active or inactive ingredient) may be embedded in or located on any of the device's components, for example, the rim 30. It is appreciated that in some cases, there may be no rim 30, so long as structural support is provided by another component of the device, e.g., the holdfast. In this case, the drug may be loaded or coated on the holdfast or within the passageway.

Figure 23:
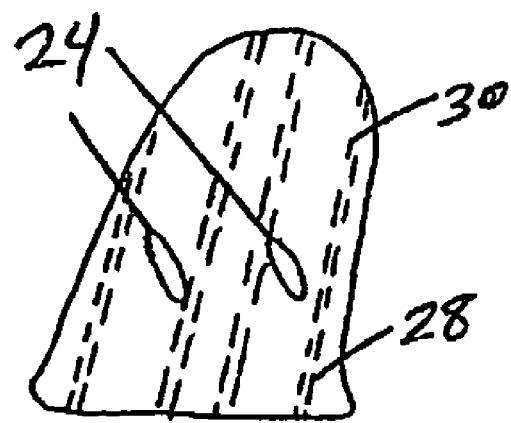
FIG. 23 is a cross-sectional view of a respiratory device where the device is removable and adapted for the nasal cavity.

FIG. 23 shows a cross-sectional view of another embodiment of a respiratory device where the device is removable and may be secured in communication with a nasal cavity. In this figure, there are two airflow passageways. Each passageway is shown with an airflow resistor 24 therein. The holdfast 28 surrounds both passageways, and each passageway includes an (optional) rim 30. Each of the flow resistors 24 may increase or decrease resistance to airflow independently and may work simultaneously or at different times during the respiratory cycle. For example, in some cases, during inhalation, one of the airflow resistors 24 may decrease resistance to airflow while the second airflow resistor 24 increases resistance to airflow. On exhalation, the first airflow resistor 24 may increase resistance to airflow while the second airflow resistor 24 decreases resistance to airflow. In other words, inspiratory airflow may proceed through one location, and expiratory airflow may proceed through a second location within the same device.

Figure 24:
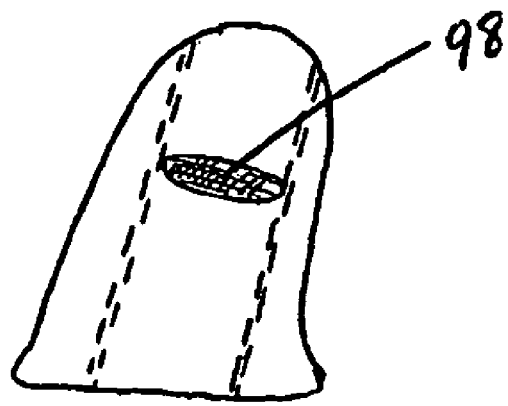
FIG. 24 is a cross-sectional view of a respiratory device where the device is removable and adapted for the nasal cavity.

FIG. 24 is a cross-sectional view of another embodiment of the respiratory device where the device is removable and may be secured in communication with a nasal cavity. The device is shown with a fixed filter 98 that is located in the path of the airflow as it traverses the device. The fixed filter 98 may help clear the airflow of any solid or liquid particles, debris, odors, allergens, pollen, and/or infectious agents. This filter 98 may remain roughly fixed in place during all parts of the respiratory cycle though some degree of movement may be permitted. A drug may be placed within or on the surface of one or more components of the device to provide additional benefit to the patient. The addition of fixed filter 98 may not lead to increased resistance in either direction, unless such a design is desired. The fixed filter 98 can be created from any number of filter materials that are known to those skilled in the art. This fixed filter 98 may be used in any of the respiratory devices herein, in addition to, or as an alternative to, an airflow resistor 4.

Figure 25:
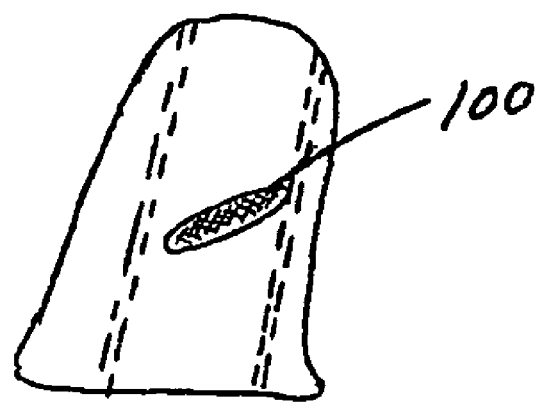
FIG. 25 is a cross-sectional view of a respiratory device where the device is removable and adapted for the nasal cavity.

FIG. 25 is a cross-sectional view of another embodiment of the respiratory device, where the device is removable and may be secured in communication with a nasal cavity. The respiratory device of FIG. 25 comprises a moveable cleansing filter 100 that is shown located within the device, and which may help to clear the airflow of solid or liquid particles, debris, odors, allergens, pollen, and/or infectious agents. In some versions, the filter may be configured to move so that it filters only during inhalation (or exhalation), or may move out of the way during periods of extremely large airflow (or air pressure) in the airflow passageway (e.g., during coughing, nose blowing, sneezing).

Figure 26A:
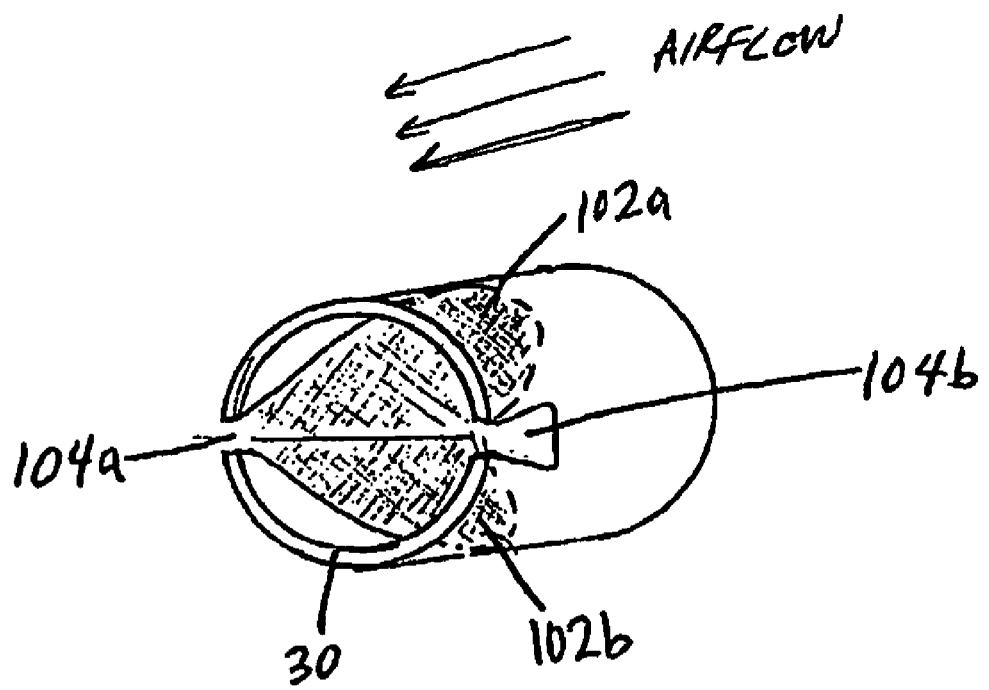
FIGS. 26a and 26b are perspective views of a respiratory device having a moveable air filter where the moveable air filter is shown during inhalation (FIG. 26a) and exhalation (FIG. 26b), respectively.
Figure 26B:
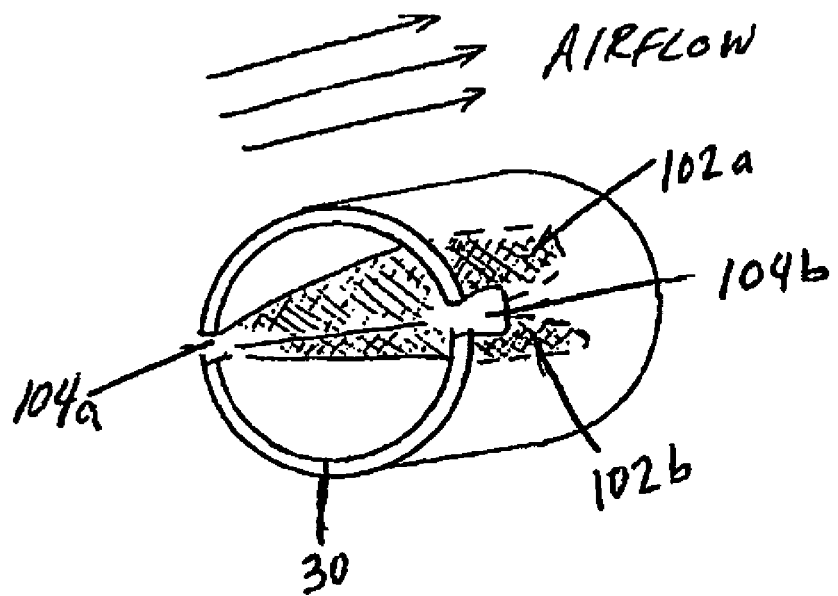

FIGS. 26a and 26b are perspective views of one version of a moveable cleansing filter where the moveable cleansing filter is shown during inhalation and exhalation respectively. A movable cleansing filter may be a movable filter, scrubber, or any other device capable of removing (particularly selectively removing) any solid or liquid particles, debris, odors, allergens, pollen, and/or infectious agents. This moveable cleansing filter may be used in any of the respiratory devices herein, in addition to, or as an alternative to, an airflow resistor 4. FIG. 26a shows the moveable cleansing filter (shown as movable filters) during inspiration (during which airflow travels from right to left in the figure) leading to displacement of moveable filter elements 102a and 102b away from one another. FIG. 26b shows the moveable cleansing filter during expiration (during which airflow travels from left to right in the figure) leading to displacement of moveable filter elements 102a and 102b towards one another. Thus, on inspiration, airflow passes through the moveable filter elements 102a and 102b and the air may be cleansed of the relevant substances. On expiration, airflow passes both through and around moveable filter elements 102a and 102b. The addition of moveable filter elements 102a and 102b ideally does not lead to increased resistance in either direction, unless such a design is desired. The moveable filter elements 102a and 102b can be created from any number of filter materials that are known to those skilled in the art. One or more openings or apertures may be placed within the moveable filter elements 102a and 102b to alter inspiratory or expiratory resistances.

Figure 27:
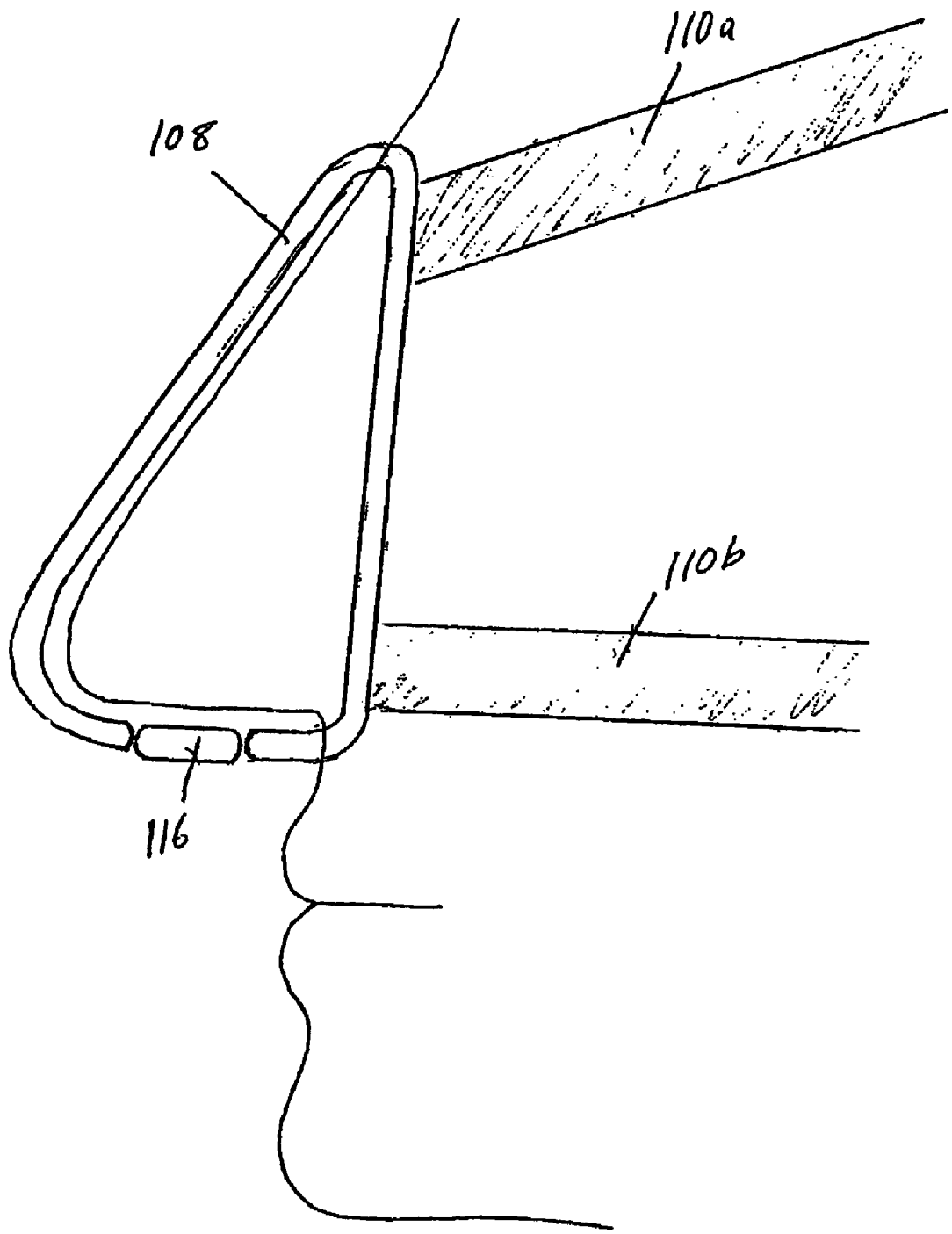
FIG. 27 is a perspective view of another respiratory device where the device is removable and adapted for the nasal cavity.

FIG. 27 is a three dimensional view of another embodiment of the subject devices where the device is removable and secured in communication with both nasal cavities. Nasal mask 108 is positioned securely against the nose and face in order to minimize or eliminate the possibility of air leak around the periphery of the device. The device includes a holdfast comprising straps 110a and 110b (that facilitate the secure positioning) and a nasal mask 108 that is secured against the face by the straps. The mask's airflow resistor 116 modulates inspiratory and/or expiratory resistance during any or all portions of the respiratory cycle. There is at least one airflow resistor 116 located on the device, though two or more airflow resistors 116 may be used (e.g., one placed in proximity to each nostril).

Figure 28:
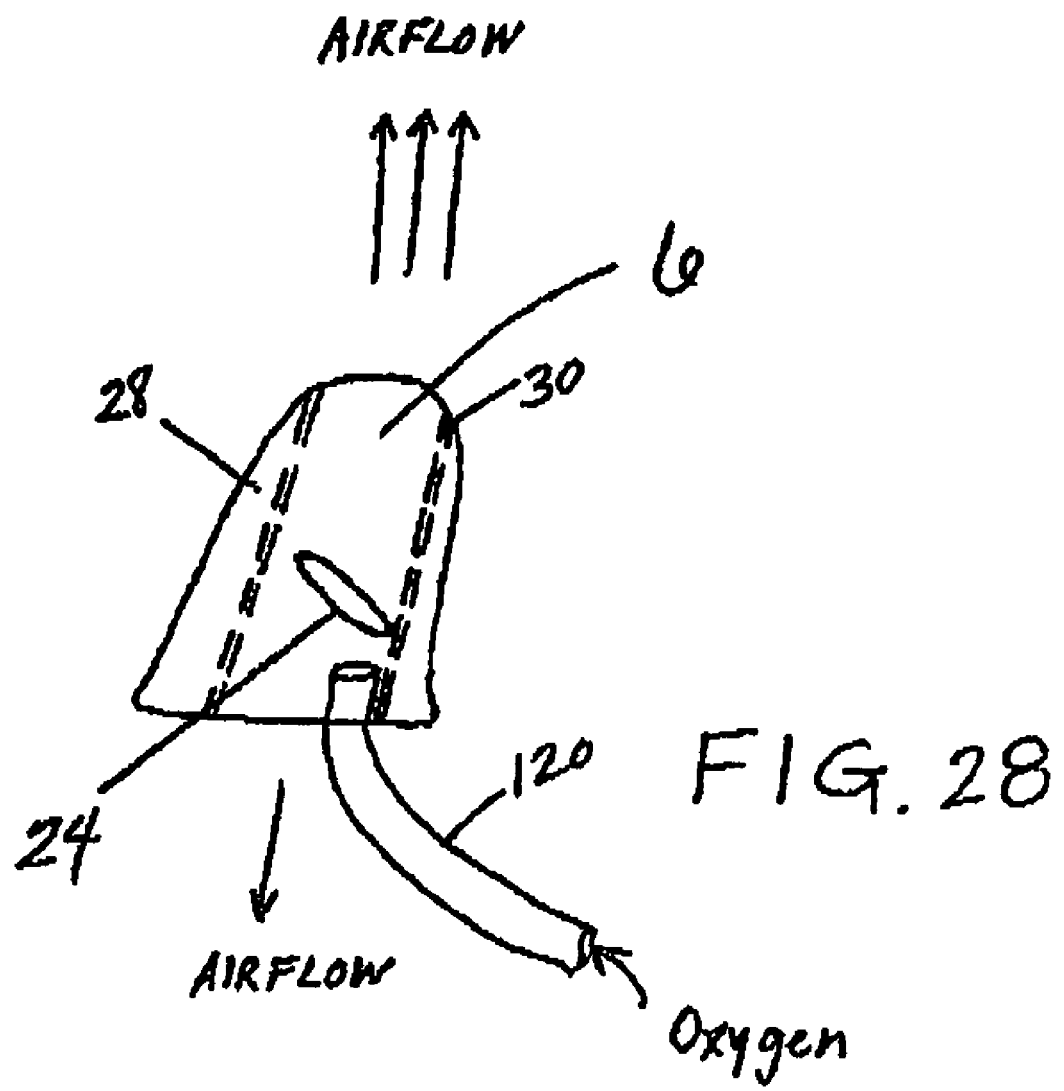
FIG. 28 shows a cross-sectional view of another respiratory device where the device is removable and adapted for the nasal cavity.

FIG. 28 is a cross-sectional view of another embodiment of the respiratory device, where the device is removable and may be secured in communication with a nasal cavity. In FIG. 28, a respiratory device further comprises a respiratory gas supply. A respiratory gas inlet 120 is shown attached to the respiratory device, providing gas, such as pure oxygen or mixed oxygen to the passageway. An airflow resistor 24 is included within the passageway which may modify inspiratory and/or expiratory resistance during any or all portions of the respiratory cycle. In some versions of the device, the airflow resistor 24 during exhalation may feature a flap mechanism in which the flap partially or completely occludes respiratory gas inlet 120, thereby only providing release of gas when the patient is inhaling and the flow resistor 24 is therefore open to some degree. The device that provides the respiratory gas may be permanently or non-permanently fixed, attached, or otherwise coupled to the holdfast, rim, or airflow resistor via a press fit, adhesive, or in some other fashion. In some cases, the respiratory gas supply may be an off-the-shelf device that that provides respiratory gas, as is currently available from multiple manufacturers.

The aforementioned devices and methods of using them may provide a first airflow resistance to airflow from proximal airways to distal airways (inhalation) and a second flow resistance to airflow from distal airways to proximal airways (expiration). In some of the respiratory devices described herein, when expiratory airflow and/or expiratory airway pressures fall below a threshold (one that is too low to keep an airflow resistor mechanism open), expiration airflow will be stopped, leading to PEEP. As a result, normal inspiration, normal expiration, and PEEP are accommodated while offering potential benefits to the patient, including clinical benefits.

Uses of the Respiratory Devices

The respiratory devices and methods described herein may be used for a variety of therapeutic and non-therapeutic purposes. A description of some of these uses is given below. The respiratory devices and methods described herein may be used in other ways as well, and these examples are not to be considered exhaustive.

Generally, the respiratory devices described herein may improve the respiratory and cardiovascular function of a person in need thereof (e.g., a patient). Thus, these respiratory devices may be used therapeutically, for example, to cure, treat or ameliorate the symptoms of a variety of medical disease states. Furthermore, the respiratory devices may be useful in generally improving the health and well being of any person.

Disease states which may be treated by the devices and methods described herein include but are not limited to: heart failure (right-sided and/or left-sided), COPD, pulmonary edema, sleep apnea (obstructive and/or central), sleep-disordered breathing, Cheyne-Stokes respiration, insomnia, snoring and other sleep disorders, asthma, bronchomalacia, acute lung injury, ARDS, cystic fibrosis, hypoxemic respiratory failure, gastroesophageal reflux disease, hiatal hernia, heartburn, hypertension, myocardial infarction, arrhythmia, cardiomyopathy, cardiac valve disease (either stenosis or regurgitation of the mitral, aortic, tricuspid, or pulmonic valves), stroke, transient ischemic attack, increased cerebral pressure, a variety of inflammatory diseases, and degenerative neurologic conditions. Moreover, the devices be beneficial for patients being weaned off mechanical ventilation, as well as post-operative patients.

The increased pressure within the airways may reduce the amount and frequency of pulmonary edema, a common consequence of heart failure. Afterload and preload on the heart may also be affected; for example, afterload and preload may be decreased in patients with heart failure. Filling pressures may be increased or, more likely, decreased. Decreasing filling pressure may potentially benefit patients with failing hearts. Gas exchange may improve in many cases, leading to increases in $pO_2$ and decreases in $pCO_2$. In some cases, the level of $pCO_2$ may actually increase or become more stable and less likely to fluctuate. This increase in the stability of $pCO_2$ levels may lead to profound benefits in patients with central sleep apnea and in patients with Cheyne-Stokes breathing, for example.

Any location within the body that is exposed to respiratory airflow (including but not limited to the upper airway, trachea, bronchi, nasopharynx, oropharynx, nasal cavity, oral cavity, vocal cords, larynx, tonsils and related structures, back of the tongue, sinuses, and turbinates) may benefit from the increased airway pressure and increased duration of expiratory airflow. In some cases, there will be a reduction in swelling andedema in these locations, leading to increased diameters of the airways and conduits in which the airflow passes. This leads to less of a tendency for these structures to collapse upon inhalation. Moreover, these structures may be less prone to create noise on inspiration or expiration, thereby reducing the quantity and/or quality of snoring. Put another way, the reduction of edema in the airways may make it less likely that these structures will collapse and may reduce the volume and frequency of snoring, apnea, or hypopnea. Furthermore, reduction in swelling and edema and improved lymphatic flow due to these positive pressures may reduce nasal congestion, inflammation, and sinusitis for example.

The respiratory device may also increase lung compliance. For example, lung compliance may increase partly if fluid which might otherwise be in the lung and alveoli is driven away by the increased airway pressure. This increased lung compliance may make it easier to breathe and may require less effort and force on the part of the patient to displace the diaphragm a certain distance to achieve a certain tidal volume. Moreover, increased lung compliance may decrease the pressure differential between the alveoli and mouth. As this pressure differential decreases, it becomes less likely that an inhalation attempt will induce a collapse of the upper airway. Thus, an increase in lung compliance may herald a reduction in the frequency or severity of obstructive sleep apnea or hypopnea episodes. Similarly, snoring frequency and severity (volume) may be reduced for similar reasons.

The respiratory device may also improve ejection fraction. This effect may be mediated via increases in intra-thoracic pressure and alterations in transmural pressures and the beneficial effects on preload and afterload on the failing heart. In addition to left-sided benefits to the heart, there may also be benefits afforded to the right side of the heart. Improving ejection fraction with the respiratory devices described herein may result in positive short- and long-term changes to the energetics and biologic properties of the heart tissue. Some of these positive changes may mimic the positive remodeling changes seen in hearts treated with various complicated cardiac support devices such as those developed by Acorn Cardiovascular (St. Paul, Minn.) and Paracor Medical (Sunnyvale, Calif.). These expiratory resistors use the patient's own intra-thoracic pressure to "support" the patient's heart. Moreover, because the support potentially provided by the respiratory devices described herein is not limited to just the ventricle, it may support the atria, which can also be severely affected by heart failure and other cardiac or pulmonary diseases. There may be reductions in left ventricular and left atrial sizes, both in the shorter and longer term. Furthermore, cardiac sympathetic activation may be reduced, and cardiac output may be increased or decreased depending on the nature of the resistance provided.

There are a variety of other beneficial effects of enhanced expiratory resistance and increases in intra-thoracic pressure that may be achieved with the respiratory devices described herein. Examples include decreased heart rate and blood pressure. There may be a reduction in the number of arrhythmias, including but not limited to atrial/supraventricular and ventricular fibrillation, atrial/supraventricular and ventricular tachycardias, heart block, and other common arrhythmias. Thus, the respiratory devices described herein may also reduce the incidence of sudden cardiac death and other cardiac disorders. Furthermore, coronary perfusion may be expected to increase. Further, expiratory resistance and increased intra-thoracic pressures may lead to improvements in gastroesophageal reflux disease (ie heartburn), gastritis, Barrett's esophagus, esophageal cancer, hiatal hernia, and other causes of diaphragmatic hernia. This effect may be mediated by the compression of the esophagus located within the thorax due to the increased intra-thoracic pressures. As a result, food and other stomach contents may no longer be able to reflux superiorly into the esophagus, which is otherwise common when patients are lying down. Furthermore, hernias (primarily hiatal) may be reduced and pushed back into the abdomen by the increased intra-thoracic pressure. The use of these respiratory devices may have beneficial effects on other gastroenterologic conditions beyond those already described.

Cardiac valve disease, including but not limited to mitral, tricuspid, pulmonic and aortic regurgitation, and mitral, tricuspid, pulmonic and aortic stenosis may also benefit from the respiratory devices described herein. In particular, the respiratory device may effect mitral regurgitation and may help prevent further annular dilatation (a byproduct of heart failure and generalized heart dilation).

Use of the respiratory devices described herein will result in a reduction in respiratory rate, which may be very helpful in diseases such as COPD, asthma, hyperventilation, and anxiety disorders including panic attacks, among others. The ratio of inspiratory time to expiratory time (I:E ratio) may be decreased with the device. Tidal volumes may increase as well. For example, in COPD, the increased resistance may facilitate improved expiratory function. This may also allow the patient to benefit from larger tidal volumes and increased minute ventilation. In embodiments in which the respiratory device creates PEEP (positive end expiratory pressure), the amount of PEEP (or resistance generated by the device) may overcome some, or all, of the intrinsic PEEP that is common in patients with COPD. In patients with COPD or other pulmonary disorders, gas exchange may improve. In this case, gas exchange refers to the removal of $CO_2$ from the body and addition of $O_2$ into the blood stream from inspired air. Thus, $pO_2$ may increase and $pCO_2$ may decrease, particularly in patients with COPD, but more generally in all patients treated with the device. Moreover, oxygen saturation may increase, reflecting an increase of oxygen binding to hemoglobin.

Other benefits offered by the respiratory device may include a reduction in diaphragm fatigue and improved efficiency of the accessory muscles of inspiration. This may make breathing significantly easier in patients with pulmonary disease, and more specifically COPD and cystic fibrosis.

As previously mentioned, the respiratory devices described herein may decrease respiratory rate. It has been shown that slowed breathing techniques can lead to a reduction in blood pressure. Thus, the device may reduce blood pressure in a patient, including patients with hypertension (systemic and pulmonary). The reduction in blood pressure may be systolic and/or diastolic. Reductions in blood pressure may be on the order of 1-70 mm Hg systolic or diastolic. This may bring the patient to normal (<140/80 mm Hg) or near normal (<160/100 mm Hg) levels. In patients who are being treated for hypertension, the device could be used as an adjunctive therapy to drugs or as a stand-alone therapy in some patients. In some versions, a respiratory device as described herein may be used for short periods (minutes, hours, or longer) over a span of days to weeks to months to offer longer term benefits for weeks or months after the cessation of therapy. Treatments may last 15 seconds to 24 hours and may be repeated over a regular or irregular interval, for example, on the order of hours to days. The devices may be worn at night or day, while awake or during sleep, to slow respiratory rate. A reduction in blood pressure and/or heart rate may be seen while the device is in place, or after the device has been removed. This may be due to hormonal influences whose effects last longer than the period in which the device is in place. More specifically, the device may work though either a sympathetic or parasympathetic pathway.

Expiratory resistance may also prolong expiratory time, which may reduce the respiratory rate. Thus, the devices described herein may be used to reduce respiratory rate. This may have benefits in treating insomnia, since it may promote a sense of relaxation in the user, through increased parasympathetic stimulation, decreased sympathetic simulation, and/other hormonal and non-hormonal effects. This may also promote a sense of well being or relaxation that may allow the user to fall asleep easier and quicker and improve sleep quality and quantity. Thus, the respiratory devices described herein represent a novel non-pharmacologic method of treating insomnia and promoting relaxation. The device may be used throughout the day and/or night to promote said relaxation and well being.

The respiratory devices described herein may also be used to treat or ameliorate disorders characterized by ineffective, non-productive, or otherwise disturbed inspiration (including but not limited to obstructive sleep apnea or restrictive pulmonary disease). For example, with the device in place, a patient may be more likely to have slightly elevated lung volumes after exhalation. Put another way, more air than normal may be present in the lungs after exhalation when using some versions of the device. Fewer alveoli may be collapsed; thus inhalation may be easier because it will require less effort to re-open the alveoli during the subsequent breath. Moreover, pulmonary congestion and pulmonary edema may also be reduced, so compliance may be improved. As a result, it may require less effort for patients to inhale. It follows that a smaller pressure differential (between the alveoli and the mouth) will be required. The smaller the pressure differential, the less likely that the patient's conducting airways (including the upper airways and pharyngeal tissues) will collapse, thus reducing the likelihood of obstructive sleep apnea, hypopnea, and snoring.

Infectious diseases may also benefit from the respiratory devices described herein. These diseases include but are not limited to pneumonia (community and hospital acquired), tuberculosis, bronchitis, HIV, and SARS.

The respiratory devices may also be useful in pulmonary or cardiac rehabilitation. For example, the device may find use in patients with chronic pulmonary disease including but not limited to chronic bronchitis, emphysema, asthma, pulmonary fibrosis, cystic fibrosis, and pulmonary hypertension. Alternatively, the devices may benefit patients with cardiac disease, including but not limited to: angina, myocardial infarction, right or left sided heart failure, cardiomyopathy, hypertension, valve disease, pulmonary embolus, and arrhythmia.

Patients with obesity may also benefit from the use of the respiratory devices described herein. Obesity can contribute to exercise intolerance partly because it increases the metabolic requirement during activity and alters ventilatory mechanics by reducing functional residual capacity (FRC) and promoting atelectasis. Obesity may also reduce cardiac reserve, since a higher than normal cardiac output response is required during physical activity. This in turn may cause systemic hypertension, which increases left ventricular afterload. Thus, the device, through its potential reduction in atelectasis and beneficial effects on FRC, cardiac output, and blood pressure may be useful in patients with obesity.

The respiratory devices may also be used by athletes, for example, during both aerobic and non-aerobic activities, partially because of the potentially beneficial direct effects on the heart and on gas exchange. In some versions, the respiratory device may be oversized, to increase the amount of inspiratory airflow, potentially increasing the amount of oxygen transmitted to the lungs for gas exchange.

The respiratory devices described herein may also be used for therapeutic and non-therapeutic effects on sleep. Sleep quality may be improved, with more slow-wave sleep, fewer arousals, and improved REM sleep. The user may have more productive sleep and may be less tired during the day. Furthermore, the beneficial effects of the device may extend beyond the period of use, and into the daytime as well, even when the device's use is limited to the night (e.g., when the user is sleeping). In some cases, sympathetic discharge may be reduced and/or parasympathetic discharge may be increased. Thus, the device may have positive benefits on the autonomic nervous system. This may offer beneficial systemic effects as well as local effects, some of which have already been described.

The respiratory devices described herein may also be used in other locations besides the nasal and oral cavities. Indeed, any location in the body that is serves as an entry or exit location for respiratory airflow or serves as a conducting airway or conduit for airflow may benefit from the use of the devices described herein. For example, a device may be used within, on the external surface of, or near a stoma site (e.g., for use in a patient after a tracheostromy).

Inflammation (which is present in a variety of disease states) may also be reduced using the respiratory device, possibly via the aforementioned parasympathetic or sympathetic mediated effects and/or effects of the vagus nerve and its stimulation. The treatment of any condition mediated by an inflammatory cytokine cascade is within the scope of the devices and methods described herein. In some embodiments, the respiratory device is used to treat a condition where the inflammatory cytokine cascade is affected through release of pro-inflammatory cytokines from a macrophage. The condition may be one where the inflammatory cytokine cascade causes a systemic reaction, such as with septic shock. Alternatively, the condition may be mediated by a localized inflammatory cytokine cascade, as in rheumatoid arthritis. Examples of conditions which may be usefully treated using the respiratory devices described herein include, but are not limited to: appendicitis, peptic, gastric or duodenal ulcers, peritonitis, pancreatitis, ulcerative, pseudomembranous, acute or ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis, alvealitis, bronchiolitis, pharyngitis, pleurisy, sinusitis, influenza, respiratory syncytial virus, herpes, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, diabetes, ankylosing spondylitis, Berger's disease, Retier's syndrome, or Hodgkins disease.

Furthermore, the respiratory devices and methods of using them may be used by or applied to a variety of different types of animals. Representative animals with which the methods and devices find use include, but are not limited to: canines; felines; equines; bovines; ovines; etc. and primates, particularly humans. The respiratory devices described herein may also be packaged for use. For example, the respiratory devices may be packaged individually or as a set (e.g., in sets of pairs, particularly in variations in which an individual device is used with each nostril). Furthermore, the packaging may be sterile, sterilizable, or clean.

Figure 29:
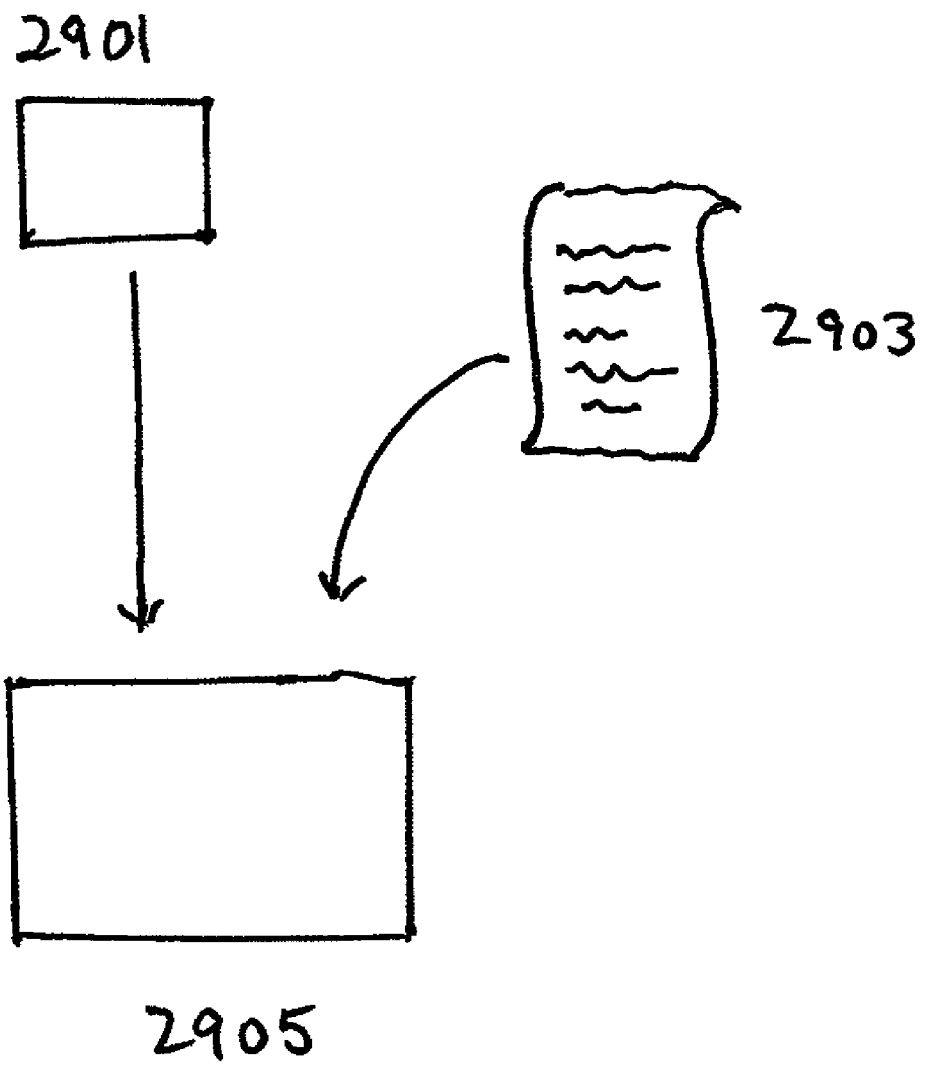
FIG. 29 shows a schematic view of a kit including a respiratory device in packaging and instructions for using the respiratory device.

The respiratory devices described herein may also be provided as part of a kit that includes at least one of the devices. FIG. 29 shows on example of a kit 2905 that includes a respiratory device (2901 illustrating a packaged respiratory device) and instructions for how to use the device 2903. The instructions 2903 are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging 2901 or sub-packaging) etc. In other embodiments, the instructions are present as an electronic storage data file present on a suitable computer readable storage medium, e.g., CD-ROM, diskette, etc. The instructions may take any form, including complete instructions on how to use the device, or references, directing a user to using additional sources for instructions (e.g., a website address with which instructions posted on the world wide web).

EXAMPLES

The following examples are offered by way of illustration and not by way of limitation.

A. Removable Application in the Oral Cavity

A respiratory device adapted for use in the oral cavity (e.g., any of the devices shown in FIGS. 1-3) may be placed into a subject's mouth by medical personnel or by the subject. The respiratory device may be secured in place by the subject's teeth, gums, tongue, lips, palate or shape of the oral cavity or surrounding anatomy including the jaw, nose, chin, or skin. The respiratory device may also (or alternatively) be secured by use of an adhesive, a securing strap, or by other holdfast. The use of an adhesive may further improve the seal between the device and the oral cavity. The device may be worn during the night or day, while the patient is awake or sleeping. In some cases, the device may be worn continuously for extended periods of time (e.g., minutes, hours, days). These devices are meant to provide benefits to subjects suffering from COPD, heart failure, sleep apnea, insomnia, hypertension, gastroesophageal reflux disease, hiatal hernia and other medical conditions mentioned previously.

In some embodiments, the device works as follows. During inhalation, the valve mechanism remains in the open position as airflow proceeds from the external environment into the airways and lungs. Open position means any position in which resistance to airflow is reduced or minimized during inhalation more than exhalation. This can be achieved using any of the airflow resistor embodiments described earlier. During exhalation, the airflow from the airways and lungs to the outside environment occurs, and an airflow resistor (e.g., a valve mechanism) subjects this exhalation airflow to greater resistance than during inhalation. Thus, resistance during inhalation is less than exhalation resistance, providing the desired effect to the subject.

B. Removable Application in the Nasal Cavity

A respiratory device adapted for use in the nasal cavity (e.g., any of the devices shown in FIGS. 4, 5, 20, and 21) may be placed into one or more of the subject's nostrils by medical personnel or by the subject himself. The respiratory device may be secured in place in the subject's nostrils by the interaction between the nostril cavity and the holdfast of the device, as shown in FIGS. 4 and 5. The use of an adhesive may further improve the seal between the device and the nasal cavity. The device may be worn during the night or day, while the patient is awake or sleeping. In some cases, the device may be worn around the clock. These devices may provide benefits to subjects suffering from COPD, heart failure, sleep apnea, insomnia, hypertension, gastroesophageal reflux disease, hiatal hernia and other medical conditions, as mentioned previously.

In some embodiments, the respiratory device worn in a nasal cavity works as follows. During inhalation, the valve mechanism remains in the open position as airflow proceeds from the external environment into the airways and lungs. Open position means any position in which resistance to airflow is reduced or minimized during inhalation more than exhalation. This may be achieved using any of the airflow resistor embodiments described earlier. During exhalation, the airflow from the airways and lungs to the outside environment occurs, and valve mechanism subjects this exhalation airflow to greater resistance than during inhalation. Thus, resistance during inhalation is less than exhalation resistance, providing the desired effect to the subject. In some versions, it may be preferable to regulate the airflow of both nostrils. For example, it may be desirable to have a single respiratory device that regulates airflow into the nasal cavity (as in FIG. 27), or to have a respiratory device that has airflow resistors for both nostrils, or to simply block all airflow through one nostril and use a respiratory device to regulate airflow through the other nostril.

C. Removable Filtering Application in the Nasal Cavity:

In one embodiment of the methods for using a respiratory device, a respiratory device as shown in either FIG. 24 or FIG. 25 is placed into one of more of the subject's nostrils by medical personnel or by the subject. The respiratory device is secured in the subject's nostrils (e.g., by the interaction between the holdfast of the device and the subject's nostrils). The use of an adhesive may further improve the seal between the device and the nasal cavity. The device can be worn during the night or day, while the patient is awake or sleeping. In some cases, the device can be worn continuously. These devices may provide benefits to subjects suffering from allergies and allergy-related diseases, sinusitis, post-nasal drip, and other medical ailments as described herein.

In some embodiments, the device works as follows. During inhalation, the fixed cleansing filter 98 or moveable cleansing filter 100 filters airflow from the external environment before it passes into the airways and lungs. During exhalation, in which airflow proceeds from the airways and lungs to the outside environment, the fixed cleansing filter 98 remains in the path of the airflow, while the moveable cleansing filter 100 may deflect or move so that less airflow passes through it (and more airflow passes around it). In either case, it may be preferable for the cleansing filter not to add any additional resistance to either inspiratory or expiratory airflow, though in some cases, that addition of resistance to inspiratory and/or expiratory airflow may be desired.

D. Removable Nostril Opening Application

In one embodiment of the methods for using a respiratory device, the device shown in FIG. 22 is placed into one of more of the subject's nostrils by medical personnel or by the subject where it is kept in place by the subject's nostrils. The device can be worn during the night or day, while the patient is awake or sleeping. In some cases, the device can be worn continuously. In this way, these devices may provide benefits to subjects suffering from sleep apnea, snoring, and other medical ailments described herein as well as to subjects desiring improved athletic performance.

In some embodiments, the device works as follows. During inhalation, the device props open the nostrils to minimize airflow resistance and to prevent the nostrils from collapsing or partially closing due to negative pressures within the nose. On exhalation, the device facilitates expiratory airflow, again by propping open the nostrils and increasing the size of the lumen available for airflow.

The respiratory devices may improve the respiratory, cardiac, and general health of the patient by mimicking the effects of pursed-lip breathing, which is adopted instinctively by many affected patients or by mimicking the expiratory resistance produced by non-invasive ventilation. Physiologically, the devices described herein may provide the same beneficial effects as those experienced in pursed-lip breathing, specifically: improving oxygen saturation; decreasing respiratory rate; and increasing tidal volume. The devices may also provide beneficial cardiac effects, including: decreased blood pressure; decreased afterload; decreased preload; decreased heart rate; and improved ejection fraction. This in turn may reduce the probability of the affected patient developing hypertension, heart failure, pulmonary edema, sleep apnea and other sequelae secondary to chronic obstructive pulmonary disease or heart failure. Furthermore, the devices may offer the significant advantage of freeing the patient from constantly pursing the lips, or having to be connected to a non-invasive ventilator via a breathing tube. In contrast to pursed-lip breathing, which cannot be performed during sleep, and non-invasive ventilation devices that are used primarily at night (and cannot be used during the performance of daily activities), these devices may provide increased expiratory resistance throughout the entire day.

Furthermore, respiratory devices may be provided for cleansing the inspired air and also for propping open the nostrils. These devices represent novel, non-invasive methods of treating diseases such as allergies, sinusitis, sleep apnea and others described herein.

All publications and patent applications cited in this specification are herein incorporated by reference in their entirety, as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A nasal respiratory device for use while sleeping and adapted to be secured so that it is disposed at least partially outside of a subject's nasal cavity, the device comprising:
   an opening configured to communicate with the nasal cavity;
   an airflow resistor in communication with the opening, wherein the airflow resistor is configured to increase the resistance to air exhaled through the opening to be more than the resistance to air inhaled through the opening; and
   a shapeable holdfast configured to seal and to secure the nasal respiratory device so that the device is disposed at least partially outside of the subject's nasal cavity.

2. The nasal respiratory device of claim 1, wherein the airflow resistor is configured to decrease the resistance to air exhaled through the opening when the airflow or air pressure differential across the airflow resistor exceeds a threshold level.

3. The nasal respiratory device of claim 1, wherein the airflow resistor is configured to increase the resistance to air exhaled through the opening when the airflow or the air pressure differential across the airflow resistor falls below a threshold level.

4. The nasal respiratory device of claim 1, wherein the airflow resistor comprises a flap valve.

5. The nasal respiratory device of claim 1, wherein the airflow resistor alters the inspiratory: expiratory ratio of a user wearing the nasal respiratory device so that the inspiratory: expiratory ratio is between about 3:1 and about 1:10.

6. The nasal respiratory device of claim 1 wherein the holdfast comprises a shape memory material.

7. The nasal respiratory device of claim 1 wherein the holdfast comprises a foam.

8. The nasal respiratory device of claim 1, further comprising a rim having sufficient strength to support the opening in the open state when at least part of the nasal respiratory device is inserted into the nasal cavity.

9. The nasal respiratory device of claim 1, wherein the holdfast comprises an adhesive configured to secure the nasal respiratory device to the subject.

10. The nasal respiratory device of claim 1 wherein the holdfast secures the nasal respiratory device in communication with both nasal cavities.

11. The nasal respiratory device of claim 1 further comprising an active agent selected from the group consisting of: a drug or medicament, and an odorant.

12. The nasal respiratory device of claim 1, wherein the airflow resistor is secured within the opening.

13. The nasal respiratory device of claim 1, wherein the holdfast at least partially surrounds the opening.

14. A kit comprising:
   a nasal respiratory device of claim 1; and
   instructions on the use of the nasal respiratory device.

15. The nasal respiratory device of claim 1, wherein the shapeable holdfast comprises a compressible holdfast configured to secure the nasal respiratory device by expanding within the subject's nasal cavity.

16. The nasal respiratory device of claim 1, wherein the shapeable holdfast comprises a compliant material.

17. The nasal respiratory device of claim 1, wherein the shapeable holdfast comprises a deformable material.

18. The nasal respiratory device of claim 1, wherein the shapeable material comprises silicone.

19. The nasal respiratory device of claim 1, wherein the shapeable holdfast is a distinct structure from the airflow resistor.

20. The nasal respiratory device of claim 1, wherein the airflow resistor is secured across the opening and configured to open from an attachment site that is not on the periphery of the opening.

21. The nasal respiratory device of claim 1, further comprising a tubular body surrounding the opening, wherein the wall of the passageway through the tubular body is parallel to a longitudinal axis through the passageway.

22. A nasal respiratory device for use while sleeping and adapted to be secured over a subject's nasal cavity, the device comprising:
   an opening configured to communicate with the subject's nasal cavity;
   an airflow resistor in communication with the opening, wherein the airflow resistor is configured to increase the resistance to air exhaled through the opening to be more than the resistance to air inhaled through the opening; and
   an adhesive holdfast configured to attach and seal the nasal respiratory device around the opening of a single nostril.

23. The nasal respiratory device of claim 22, further comprising a rim supporting the opening.

24. The nasal respiratory device of claim 22, wherein the holdfast is configured to secure to at least a portion of the subject's nose.

25. The nasal respiratory device of claim 22, wherein the airflow resistor comprises a flap valve.

26. The nasal respiratory device of claim 22, wherein the adhesive holdfast is configured to secure the nasal respiratory device at least partially over the subject's nasal cavity so that the nasal respiratory device does not substantially contact the inside of the nasal cavity.

27. A nasal respiratory device for use while sleeping and adapted to be secured so that it is disposed at least partly outside a subject's nasal cavity, the device comprising:
   a passageway configured to communicate with a subject's nasal cavity;
   a rim having sufficient strength to support the passageway in the open state when the nasal respiratory device is inserted into the nasal cavity;
   an airflow resistor in communication with the passageway, wherein the airflow resistor inhibits exhalation more than inhalation; and
   a compressible holdfast to seal and secure the nasal respiratory device so that the device is disposed at least partly outside a subject's nasal cavity, wherein the holdfast comprises a compressible material.

28. The nasal respiratory device of claim 27, wherein the holdfast comprises a shape memory material foam.

29. The nasal respiratory device of claim 27, wherein the airflow resistor comprises a flap valve.

30. The nasal respiratory device of claim 27, wherein the rim is configured so that the rim does not form a complete seal within a subject's nasal cavity.

31. A nasal respiratory device for use while sleeping and adapted to be secured at least partially outside a subject's nasal cavity comprising:

an opening configured to communicate with the nasal cavity;

an airflow resistor in communication with the opening configured to increase the resistance to air exhaled through the opening to be more than the resistance to air inhaled through the opening; and an adhesive holdfast configured to attach and seal the nasal respiratory device around the opening of a single nostril without covering the subject's mouth.

* * * * *